United States Patent
Maity et al.

(10) Patent No.: US 12,415,773 B1
(45) Date of Patent: Sep. 16, 2025

(54) METHOD OF DIMETHYL CARBONATE PRODUCTION

(71) Applicant: King Fahd University of Petroleum and Minerals, Dhahran (SA)

(72) Inventors: Niladri Maity, Dhahran (SA); Samiyah Abdullaziz Al-Jendan, Al-ahasa (SA); Ea Jaseer, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 19/217,196

(22) Filed: May 23, 2025

(51) Int. Cl.
| | |
|---|---|
| C07C 68/04 | (2006.01) |
| B01J 27/02 | (2006.01) |
| B01J 27/24 | (2006.01) |
| B01J 35/30 | (2024.01) |
| B01J 35/39 | (2024.01) |
| B01J 35/45 | (2024.01) |
| B01J 35/58 | (2024.01) |
| B01J 35/61 | (2024.01) |
| B01J 35/63 | (2024.01) |
| B01J 37/04 | (2006.01) |
| B01J 37/06 | (2006.01) |
| B01J 37/08 | (2006.01) |
| C07C 68/00 | (2020.01) |

(52) U.S. Cl.
CPC .............. *C07C 68/00* (2013.01); *B01J 27/02* (2013.01); *B01J 27/24* (2013.01); *B01J 35/393* (2024.01); *B01J 35/45* (2024.01); *B01J 35/58* (2024.01); *B01J 35/613* (2024.01); *B01J 35/635* (2024.01); *B01J 37/04* (2013.01); *B01J 37/06* (2013.01); *B01J 37/088* (2013.01)

(58) Field of Classification Search
CPC ......... C07C 68/04; B01J 35/45; B01J 35/393; B01J 35/613; B01J 27/02; B01J 27/24
See application file for complete search history.

(56) References Cited

FOREIGN PATENT DOCUMENTS

| | | |
|---|---|---|
| CN | 115322097 B | 6/2023 |
| CN | 116747799 A | 9/2023 |
| CN | 119034751 A | 11/2024 |
| JP | 5738206 B2 | 6/2015 |
| TW | 201004703 A | 2/2010 |

OTHER PUBLICATIONS

Daniel et al. Discovery of very active catalysts for methanol carboxylation into DMC by screening of a large and diverse catalyst library. New Journal of Chemistry, vol. 44, 6312-6320. (Year: 2020).*
Tomishige et al. Catalytic function of CeO2 in non-reductive conversion of CO2 with alcohols. Materials Today Sustainability, vol. 9, 1-12. (Year: 2020).*
Na Liu, et al., "Zn-Doped CeO2 Nanorods: a Highly Efficient Heterogeneous Catalyst for the Direct Synthesis of Dimethyl Carbonate from CO2 and Methanol", Chemistry Select, vol. 8, Issue 3, Jan. 19, 2023, e202203472, 14 pages.

* cited by examiner

*Primary Examiner* — Sikarl A Witherspoon
(74) *Attorney, Agent, or Firm* — Oblon, McClelland, Maier &Neustadt, L.L.P.

(57) ABSTRACT

A method of dimethyl carbonate production includes reacting $CO_2$ and methanol in the presence of a heteroatom-modified cerium oxide catalyst to form dimethyl carbonate. The heteroatom-modified cerium oxide catalyst includes an element selected from the group consisting of N, S and combinations thereof, in an amount ranging from 0.05 to 2 wt. % based on the total weight of the heteroatom-modified cerium oxide catalyst. The heteroatom-modified cerium oxide catalyst is in the form of nanorods with an average diameter in a range from 1 to 50 nm and an average length in a range from 10 to 700 nm. The dimethyl carbonate yield is greater than or equal to 40 $mmol \cdot g_{catalyst}^{-1}$.

20 Claims, 27 Drawing Sheets

METHOD OF DIMETHYL CARBONATE PRODUCTION

STATEMENT REGARDING PRIOR DISCLOSURE BY THE INVENTORS

Aspects of the present disclosure are described in Maity, N. et al., "Heteroatom-assisted oxygen vacancies in cerium oxide catalysts for efficient synthesis of dimethyl carbonate from $CO_2$ and methanol" published in Issue 22, Catalysis Science and Technology, which is incorporated herein by reference in its entirety.

STATEMENT OF ACKNOWLEDGEMENT

Support provided by the Interdisciplinary Research Center for Refining and Advanced Chemicals, King Fahd University of Petroleum & Minerals, Saudi Arabia, through projects INRC2310 and INRC2421 is gratefully acknowledged.

BACKGROUND

Technical Field

The present disclosure is directed towards a method of manufacturing dimethyl carbonate, and more particularly, a method of manufacturing dimethyl carbonate from $CO_2$ and methanol as a green synthetic route.

Description of Related Art

The "background" description provided herein is for the purpose of generally presenting the context of the disclosure. The work of the presently named inventors, to the extent it is described in this background section, as well as aspects of the description which may not otherwise qualify as prior art at the time of filing, are neither expressly nor impliedly admitted as prior art against the present disclosure.

The continuous rise in atmospheric carbon dioxide ($CO_2$) levels has become a pressing environmental concern, demanding immediate and innovative strategies to mitigate climate change. Among various approaches, the catalytic conversion of $CO_2$ into value-added chemicals has gained increased attention, although the thermodynamic stability of $CO_2$ presents major challenges to its activation and transformation. While industrial applications utilizing $CO_2$ for producing chemicals like urea, salicylic acid, polycarbonates, and cyclic carbonates exist, the scope remains limited.

Dimethyl carbonate (DMC) is recognized as a valuable chemical due to its eco-friendly profile and wide-ranging applications, including its role as a methylating agent, fuel additive, and electrolyte component in lithium-ion batteries. Conventional DMC synthesis methods involve hazardous reagents and face economic and safety limitations. Direct synthesis of DMC from $CO_2$ and methanol has emerged as a greener alternative but suffers from low yields due to thermodynamic constraints and by-product formation. Various techniques, such as employing chemical and physical dehydrating agents, membrane reactors, and different catalyst systems, have been explored to enhance DMC production, with solid oxides like $CeO_2$ showing particular promise. Furthermore, strategies such as metal and heteroatom doping have been investigated to modulate the surface properties and defect chemistry of $CeO_2$, broadening its application across multiple catalytic applications. However, there remains a need for further advancements in material design to improve catalytic efficiency for sustainable DMC synthesis under moderate conditions.

Each of the aforementioned synthesis methods suffers from one or more drawbacks hindering their adoption. Accordingly, it is one object of the present disclosure to provide a synthesis method and system that may circumvent the drawbacks, such as complexity, high cost, lack of multi-phase integration and nanoscale precision, of the materials known in the art.

SUMMARY

In an exemplary embodiment, a method of dimethyl carbonate production is described. The method includes reacting $CO_2$ and methanol in the presence of a heteroatom-modified cerium oxide catalyst to form dimethyl carbonate. The heteroatom-modified cerium oxide catalyst includes an element selected from the group consisting of N, S and combinations thereof, in an amount ranging from 0.05 to 2 wt. % based on the total weight of the heteroatom-modified cerium oxide catalyst. The heteroatom-modified cerium oxide catalyst is in the form of nanorods with an average diameter in a range from 1 to 50 nanometer (nm) and an average length in a range from 10 to 700 nm. The dimethyl carbonate yield is greater than or equal to 40 millimoles per gram of catalyst ($mmol \cdot g_{catalyst}^{-1}$).

In some embodiments, the heteroatom-modified cerium oxide catalyst includes N in an amount ranging from 0.1 to 0.5 wt. % based on the total weight of the heteroatom-modified cerium oxide catalyst.

In some embodiments, the heteroatom-modified cerium oxide catalyst includes N in an amount ranging from 0.15 to 0.35 wt. % based on the total weight of the heteroatom-modified cerium oxide catalyst.

In some embodiments, the heteroatom-modified cerium oxide catalyst includes S in an amount ranging from 0.1 to 1 wt. % based on the total weight of the heteroatom-modified cerium oxide catalyst.

In some embodiments, the heteroatom-modified cerium oxide catalyst includes S in an amount ranging from 0.15 to 0.5 wt. % based on the total weight of the heteroatom-modified cerium oxide catalyst.

In some embodiments, the dimethyl carbonate yield is greater than or equal to 60 millimoles per gram ($mmol \cdot g^{-1}$).

In some embodiments, the dimethyl carbonate yield is greater than or equal to 80 $mmol \cdot g^{-1}$.

In some embodiments, the dimethyl carbonate yield is greater than or equal to 100 $mmol \cdot g^{-1}$.

In some embodiments, the dimethyl carbonate yield is greater than or equal to 120 $mmol \cdot g^{-1}$.

In some embodiments, the selectivity for dimethyl carbonate is greater than or equal to 94%.

In some embodiments, the selectivity for dimethyl carbonate is greater than or equal to 97.5%.

In some embodiments, the selectivity for dimethyl carbonate is greater than or equal to 99%.

In some embodiments, the heteroatom-modified cerium oxide catalyst is in the form of nanorods with an average diameter in a range from 5 to 30 nm and an average length in a range from 50 to 500 nm.

In some embodiments, the heteroatom-modified cerium oxide catalyst is in the form of nanorods with an average diameter in a range from 10 to 25 nm and an average length in a range from 75 to 300 nm.

In some embodiments, the Brunauer-Emmett-Teller (BET) surface area of the heteroatom-modified cerium oxide catalyst is greater than or equal to 65 $m^2/g$.

In some embodiments, the BET surface area of the heteroatom-modified cerium oxide catalyst is greater than or equal to 75 $m^2/g$.

In some embodiments, the BET surface area of the heteroatom-modified cerium oxide catalyst is greater than or equal to 85 $m^2/g$.

In some embodiments, the pore volume of the heteroatom-modified cerium oxide catalyst is greater than or equal to 0.4 $cm^3/g$.

In some embodiments, the pore volume of the heteroatom-modified cerium oxide catalyst is greater than or equal to 0.5 $cm^3/g$.

In some embodiments, the pore volume of the heteroatom-modified cerium oxide catalyst is greater than or equal to 0.6 $cm^3/g$.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
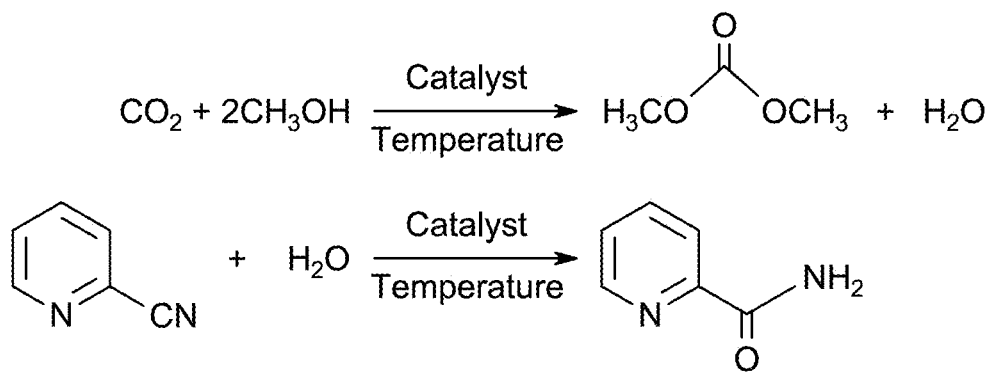
FIG. 1 is a schematic diagram of the production of dimethyl carbonate (DMC) from methanol ($CH_3OH$) and $CO_2$ involving the use of 2-cyanopyridine (2-CP) as a dehydrating agent, according to certain embodiments.

When describing the present disclosure, the terms used are to be construed in accordance with the following definitions, unless a context dictates otherwise.

Embodiments of the present disclosure will now be described more fully hereinafter with reference to the accompanying drawings wherever applicable, in that some, but not all, embodiments of the disclosure are shown.

In the drawings, like reference numerals designate identical or corresponding parts throughout the several views. Further, as used herein, the words 'a,' 'an' and the like generally carry a meaning of 'one or more,' unless stated otherwise.

Furthermore, the terms 'approximately,' 'approximate,' 'about,' and similar terms generally refer to ranges that include the identified value within a margin of 20%, 10%, or preferably 5%, and any values therebetween.

As used herein, the term 'room temperature' refers to a temperature range of '25 degrees Celsius (° C.)±3° C. in the present disclosure.

As used herein, the term 'lattice parameter' refers to a physical dimension that defines the size of the unit cell in a crystal lattice, typically expressed in angstroms (Å), and indicative of structural changes or dopant incorporation in crystalline materials.

As used herein, the term 'crystallite size' refers to the average size of coherently diffracting domains in a crystalline material, often determined using X-ray diffraction techniques through the Scherrer equation.

As used herein, the term 'surface basicity' refers to the concentration and strength of basic sites on a catalyst surface, which can interact with acidic molecules like $CO_2$ and is typically measured by $CO_2$-temperature programmed desorption (TPD).

As used herein, the term 'surface acidity' refers to the concentration and strength of acidic sites on a catalyst surface, which can activate nucleophilic species such as methanol and is generally evaluated by $NH_3$-temperature programmed desorption (TPD).

As used herein, the term 'dimethyl carbonate yield' refers to the amount of DMC produced per unit mass of catalyst under given reaction conditions, typically expressed in $mmol \cdot g_{catalyst}^{-1}$.

As used herein, the term 'dimethyl carbonate selectivity' refers to the percentage of methanol converted that results in the formation of DMC, relative to all products formed, indicating the efficiency of the catalytic process.

A weight percent of a component, unless specifically stated to the contrary, is based on the total weight of the formulation or composition in which the component is included. For example, if a particular element or component in a composition or article is said to have 5 wt. %, it is understood that this percentage is in relation to a total compositional percentage of 100%.

The present disclosure is intended to include all hydration states of a given compound or formula, unless otherwise noted or when heating a material.

An aspect of the present disclosure is directed to synthesis of dimethyl carbonate (DMC) from $CO_2$ and methanol in presence of heteroatom (N and S) modified $CeO_2$ nanorod catalysts exhibiting enhanced surface properties and activity under moderate conditions.

A method of dimethyl carbonate production is described. The method includes reacting $CO_2$ and methanol in the presence of a heteroatom-modified cerium oxide catalyst to form dimethyl carbonate. In some embodiments, dehydrating agents may be present during the reacting that may include, but are not limited to, sulfuric acid, phosphoric acid, polyphosphoric acid, acetic anhydride, trifluoroacetic anhydride, thionyl chloride, phosphorus pentoxide, aluminum chloride, zinc chloride, calcium chloride, magnesium sulfate, sodium sulfate, silica gel, molecular sieves, boron trifluoride, titanium tetrachloride, ferric chloride, dimethylformamide (DMF), dimethyl sulfoxide (DMSO), oxalyl chloride, tosyl chloride, sodium polyacrylate, potassium polyacrylate, methanesulfonyl chloride, trifluoromethanesulfonic anhydride, carbonyldiimidazole (CDI), dicyclohexylcarbodiimide (DCC), N,N'-diisopropylcarbodiimide (DIC), chlorosulfonic acid, acetyl chloride, benzoyl chloride, and trimethyl orthoformate. In a preferred embodiment, dehydrating agent 2-cyanopyridine is present.

In some embodiments, the heteroatom-modified cerium oxide catalyst includes elements selected from the group consisting of phosphorus, boron, fluorine, chlorine, bromine, iodine, silicon, selenium, tellurium, arsenic, antimony, and carbon. In a preferred embodiment, the heteroatom-modified cerium oxide catalyst includes heteroatom elements N, S and combinations thereof, in an amount ranging from 0.01 to 5 wt. %, preferably 0.05 to 2 wt. %, preferably 0.08 to 2 wt. %, preferably 0.1 to 1.8 wt. %, preferably 0.12 to 1.4 wt. %, preferably 0.14 to 1 wt. %, preferably 0.15 to 0.5 wt. %, preferably 0.15 to 0.35 wt. % based on the total weight of the heteroatom-modified cerium oxide catalyst.

In some embodiments, the heteroatom-modified cerium oxide catalyst includes N in an amount ranging from 0.05 to 2.5 wt. %, preferably 0.1 to 0.5 wt. %, preferably 0.2 to 0.5 wt. %, preferably 0.3 to 0.5 wt. %, preferably 0.4 to 0.5 wt. %, preferably 0.15 to 0.35 wt. % based on the total weight of the heteroatom-modified cerium oxide catalyst. In a preferred embodiment, the heteroatom-modified cerium oxide catalyst includes N in amount of 0.30 wt. % based on the total weight of the heteroatom-modified cerium oxide catalyst. In another preferred embodiment, the heteroatom-modified cerium oxide catalyst includes N in amount of 0.20 wt. % based on the total weight of the heteroatom-modified cerium oxide catalyst.

In some embodiments, the heteroatom-modified cerium oxide catalyst includes S in an amount ranging from 0.05 to 2.5 wt. %, preferably 0.075 to 1 wt. %, preferably 0.1 to 0.8 wt. %, preferably 0.12 to 0.6 wt. %, preferably 0.15 to 0.5 wt. %, preferably 0.18 to 0.46 wt. %, based on the total weight of the heteroatom-modified cerium oxide catalyst. In a preferred embodiment, the heteroatom-modified cerium oxide catalyst includes S in an amount of 0.46 wt. % based on the total weight of the heteroatom-modified cerium oxide catalyst. In another preferred embodiment, the heteroatom-modified cerium oxide catalyst includes S in an amount of 0.18 wt. % based on the total weight of the heteroatom-modified cerium oxide catalyst.

In some embodiments, the catalyst includes nanorod morphologies, although other morphologies such as nanosheets, nanowires, nanospheres, nanocrystals, nanorectangles, nanotriangles, nanopentagons, nanohexagons, nanoprisms, nanodisks, nanocubes, nanoribbons, nanoblocks, nanotoroids, nanodiscs, nanobarrels, nanogranules, nanowhiskers, nanoflakes, nanofoils, nanopowders, nanoboxes, nanobeads, nanobelts, nano-urchins, nanoflowers, nanostars, tetrapods, and their mixtures thereof are also possible. In a preferred embodiment, the heteroatom-modified cerium oxide catalyst is in the form of nanorods. In some embodiments, the heteroatom-modified cerium oxide nanorods have an average diameter in a range from 0.5 to 100 nm, preferably 1 to 50 nm, preferably 3 to 45 nm, preferably 5 to 40 nm, preferably 7.5 to 35 nm, preferably 10 to 30 nm, preferably 10 to 25 nm. In some embodiments, the heteroatom-modified cerium oxide nanorods have an average length in a range from 5 to 1000 nm, preferably 10 to 700 nm, preferably 20 to 700 nm, preferably 30 to 650 nm, preferably 40 to 600 nm, preferably 50 to 500 nm, preferably 75 to 300 nm.

In some embodiments, the catalyst material may include crystalline phases, but is not limited to Quartz, Calcite, Hematite, Magnetite, Goethite, Dolomite, Albite, Anorthite, Pyrite, Fluorite, Halite, Barite, Apatite, Rutile, and Zircon. In a preferred embodiment, the heteroatom-modified cerium oxide nanorods has cubic fluorite structure with the space group Fm3m. In some embodiments, lattice parameter determined from PXRD may vary from 0.5 to 10 Å, preferably 1 to 6 Å, preferably 2 to 6 Å, preferably 3 to 6 Å, preferably 4 to 6 Å, preferably 5 to 6 Å. In a preferred embodiment, lattice parameter of the cerium oxide catalyst is 5.427 Å, the sulfur-modified cerium oxide catalyst is 5.429 Å, and the nitrogen-modified cerium oxide catalyst is 5.433 Å. In some embodiments, crystallite size determined from PXRD may vary from 0.5 to 20 nm, preferably 1 to 15 nm, preferably 2 to 15 nm, preferably 3 to 15 nm, preferably 4 to 13 nm, preferably 5 to 12 nm, preferably 6 to 12 nm, preferably 7 to 11 nm, preferably 8 to 11 nm, preferably 9 to 11 nm. In a preferred embodiment, the crystallite size of the cerium oxide catalyst is 10.4 nm, the sulfur-modified cerium oxide catalyst is 9.9 nm, and the nitrogen-modified cerium oxide catalyst is 10.1 nm.

In some embodiments, surface basicity due to adsorbed $CO_2$ of heteroatom-modified cerium oxide nanorods may range from 0.005 to 2 mmol/g, preferably 0.01 to 1 mmol/g, preferably 0.02 to 0.5 mmol/g, preferably 0.03 to 0.4 mmol/g, preferably 0.04 to 0.3 mmol/g, preferably 0.05 to 0.2 mmol/g, preferably 0.06 to 0.2 mmol/g, preferably 0.07 wt. mmol/g, preferably 0.08 to 0.15 mmol/g, preferably 0.9 to 0.14 mmol/g. In a preferred embodiment, the surface basicity of the cerium oxide catalyst is 0.109 mmol/g, the surface basicity of the sulfur-modified cerium oxide catalyst is 0.113 mmol/g, and the surface basicity of the nitrogen-modified cerium oxide catalyst is 0.130 mmol/g. In some embodiments, surface acidity due to adsorbed $NH_3$ of heteroatom-modified cerium oxide nanorods may range from 0.05 to 0.6 mmol/g, preferably 0.1 to 0.5 mmol/g, preferably 0.12 to 0.4 mmol/g, preferably 0.13 to 0.4 mmol/g. In a preferred embodiment, the surface acidity of the cerium oxide catalyst is 0.290 mmol/g, the sulfur-modified cerium oxide catalyst is 0.324 mmol/g, and the nitrogen-modified cerium oxide catalyst is 0.130 mmol/g.

In some embodiments, the atomic concentration of $Ce^{3+}$ in the catalyst determined from XPS may range from 5 to 60%, preferably 10 to 50%, preferably 12 to 40%, preferably 13 to 30%, preferably 15 to 25%, preferably 17 to 22%, based on the total number of atoms in the catalyst. In a preferred embodiment, $Ce^{3+}$ the atomic concentration of the cerium oxide catalyst is 17.8%, the sulfur-modified cerium oxide catalyst atomic concentration is 20.4%, and the nitrogen-modified cerium oxide catalyst atomic concentration is 21.8% based on the total number of atoms in the catalyst.

In some embodiments, the Brunauer-Emmett-Teller (BET) surface area of the heteroatom-modified cerium oxide catalyst is greater than or equal to 40 m$^2$/g, preferably greater than or equal to 65 m$^2$/g, preferably greater than or equal to 67 m$^2$/g, preferably greater than or equal to 70 m$^2$/g, preferably greater than or equal to 75 m$^2$/g, preferably greater than or equal to 77 m$^2$/g, preferably greater than or equal to 80 m$^2$/g, preferably greater than or equal to 85 m$^2$/g. In a preferred embodiment, the BET surface area of the cerium oxide catalyst is 85 m$^2$/g, the BET surface area of the sulfur-modified cerium oxide catalyst is 87 m$^2$/g, and BET surface area of the nitrogen-modified cerium oxide catalyst is 86 m$^2$/g.

In some embodiments, the pore volume of the heteroatom-modified cerium oxide catalyst is greater than or equal to 0.2 cm$^3$/g, preferably greater than or equal to 0.4 cm$^3$/g, preferably greater than or equal to 0.45 cm$^3$/g, preferably greater than or equal to 0.5 cm$^3$/g, preferably greater than or equal to 0.55 cm$^3$/g, preferably greater than or equal to 0.6 cm$^3$/g. In a preferred embodiment, the pore volume of the cerium oxide catalyst is 0.405 cm$^3$/g, the pore volume of the sulfur-modified cerium oxide catalyst is 0.509 cm$^3$/g, and the pore volume of the nitrogen-modified cerium oxide catalyst is 0.648 cm$^3$/g.

In some embodiments, the dimethyl carbonate yield is greater than or equal to 20 mmol·g$_{catalyst}^{-1}$, preferably greater than or equal to 40 mmol·g$_{catalyst}^{-1}$, preferably greater than or equal to 50 mmol·g$_{catalyst}^{-1}$, preferably greater than or equal to 60 mmol·g$_{catalyst}^{-1}$, preferably greater than or equal to 70 mmol·g$_{catalyst}^{-1}$, preferably greater than or equal to 80 mmol·g$_{catalyst}^{-1}$, preferably greater than or equal to 90 mmol g$_{catalyst}^{-1}$, preferably greater than or equal to 100 mmol·g$_{catalyst}^{-1}$, preferably greater than or equal to 110 mmol·g$_{catalyst}^{-1}$, preferably greater than or equal to 120 mmol·g$_{catalyst}^{-1}$. In a preferred embodiment, the dimethyl carbonate yield of the cerium oxide catalyst is 28.8 mmol·g$_{catalyst}^{-1}$, the sulfur-modified cerium oxide catalyst is 49.7 mmol·g$_{catalyst}^{-1}$, and the nitrogen-modified cerium oxide catalyst is 113.3 mmol·g$_{catalyst}^{-1}$.

In some embodiments, reaction temperature for synthesis of DMC may range from 25 to 250° C., preferably 50 to 200° C., preferably 60 to 175° C., preferably 70 to 150° C., preferably 80 to 130° C., preferably 90 to 110° C. In a preferred embodiment, the reaction temperature is 100° C. In some embodiments, reaction time for synthesis of DMC may range from 0.5 to 30 h, preferably 1 to 25 h, preferably 1 to 25 h, preferably 1 to 15 h, preferably 1 to 10 h, preferably 1.5 to 5 h. In a preferred embodiment, reaction time is 2 hours. In some embodiments, $CO_2$ pressure may range from 0.05 to 10 MPa, preferably 0.1 to 8 MPa, preferably 1 to 7 MPa, preferably 2 to 6 MPa, preferably 3 to 5 MPa, preferably 3.5 to 4.5 MPa. In a preferred embodiment, $CO_2$ pressure is 4 MPa.

In some embodiments, the selectivity for dimethyl carbonate is greater than or equal to 94%, preferably greater than or equal to 95%, preferably greater than or equal to 96%, preferably greater than or equal to 97%, preferably greater than or equal to 97.5%, preferably greater than or equal to 98%, preferably greater than or equal to 99%. In a preferred embodiment, the selectivity for dimethyl carbonate of the cerium oxide catalyst is 100%, the selectivity for dimethyl carbonate of the sulfur-modified cerium oxide catalyst is 100%, and the selectivity for dimethyl carbonate of the nitrogen-modified cerium oxide catalyst is 100%.

The following examples are provided solely for illustration and are not to be construed as limitations of the present disclosure, as many variations thereof are possible without departing from the spirit and scope of the present disclosure.

EXAMPLES

The following examples demonstrate a method of dimethyl carbonate production. The examples are provided solely for illustration and are not to be construed as limitations of the present disclosure, as many variations thereof are possible without departing from the spirit and scope of the present disclosure.

Example 1: Materials

All the chemicals, such as $Ce(NO_3)_3 \cdot 6H_2O$, NaOH, urea, thiourea, methanol, 2-cyanopyridine, p-xylene purchased from Sigma-Aldrich were used as received without further purification. However, the cerium nanopowder ($CeO_2$-NP; CAS No. 1306-38-3, Product No. 700290-25G, Sigma-Aldrich) was calcined at 600° C. before the utilization.

Example 2: Synthesis of $CeO_2$ Nanorod Material

The $CeO_2$ nanorod ($CeO_2$-NR) catalyst was synthesized using a hydrothermal method. In the typical synthesis process for $CeO_2$-NR, 0.004 mol of $Ce(NO_3)_3 \cdot 6H_2O$ (1.736 g) was dissolved in 10 ml of water within a 100 ml Teflon-lined stainless steel autoclave. Simultaneously, 0.48 mol of NaOH (19.2 g) was dissolved in 70 ml of deionized water and added to the Teflon-lined stainless-steel autoclave, where the mixture underwent stirring for 30 minutes. Subsequently, the autoclave was securely sealed and transferred to an oven maintained at 100° C. for 24 h. After cooling to room temperature under ambient conditions the resulting solid was separated using a centrifuge instrument. The solid was thoroughly washed with water and ethanol until the pH reached 7 and dried at 80° C. for 12 h. Finally, the material was calcined at 600° C. (5° C./min) for 4 h under air.

For the preparation of N-$CeO_2$-nanorod and S-$CeO_2$-nanorod materials (X-$CeO_2$-NR; X=S or N), urea or thiourea (0.0015 mol) was added respectively into the aqueous solution of $Ce(NO_3)_3 \cdot 6H_2O$. The rest of the synthesis steps were kept unchanged. The loading of S and N in X-$CeO_2$-NR was determined using elemental microanalysis (Table 1).

TABLE 1

Elemental microanalysis of nanorod catalysts

| Compound | Treated temperature (° C.) | Wt. (%) N | Wt. (%) S |
|---|---|---|---|
| $CeO_2$-NR | 80 | — | — |
| $CeO_2$-NR | 600 | — | — |
| S—$CeO_2$-NR | 80 | — | 0.46 |
| S—$CeO_2$-NR | 600 | — | 0.18 |
| N—$CeO_2$-NR | 80 | 0.30 | — |
| N—$CeO_2$-NR | 600 | 0.20 | — |

Example 3: Characterization of $CeO_2$ Nanorod Material

A series of following characterization techniques were employed to investigate the structural information of the $CeO_2$-nanorod materials.

The percentage of nitrogen and sulfur in the synthesized $CeO_2$ nanomaterials were analyzed by the Elemental CHNS analyzer-Vario Micro Cube.

Rigaku Miniflex II XRD with Cu-Kα radiation (λ=1.5405 Å) was utilized to determine the phase composition and crystalline structure of the catalyst. The range of 2θ diffraction angle was 5.0-90°, with a step size of 0.02 and a 2°/min scan speed. The average crystallite size (D) of the nanomaterials was determined by applying the Debye-Scherrer equation: D=Kλ/(B cos θ), where K represents the Scherrer constant (0.89), λ denotes the X-ray wavelength (0.154 nm), β stands for the full-width at half-maxima of the diffraction peak, and θ represents the diffraction angle [Scherrer, P., *Kolloidchemie Ein Lehrbuch*, 1912, 387-409, incorporated herein by reference in its entirety]. The interplanar spacings (d) were calculated using Bragg's equation nλ=2d Sin θ, where n represents diffraction order, λ and θ are as defined earlier.

Micromeritics ASAP 2020 equipment was employed to measure Brunauer-Emmett-Teller (BET) specific surface area, and pore volume through $N_2$ adsorption-desorption isotherms.

The JEOL-JEM 2100 electron microscope was employed to capture high-resolution transmission electron microscopy (HR-TEM) images. The samples were prepared by subjecting the nanomaterials to sonication in ethanol, and subsequently, the resulting suspension was carefully deposited onto carbon-coated copper grids.

Horiba Lab Ram equipped with 633 nm laser was utilized to acquire Raman spectra in the range of 200-1500 cm$^{-1}$. To estimate oxygen vacancies in $CeO_2$ materials the method reported in the literature was employed based on the half-width at half-maximum (for the scanning range of 300-600 nm) of the characteristic Raman peaks [Paick, J., et al., Effective Atomic N Doping on $CeO_2$ Nanoparticles by Environmentally Benign Urea Thermolysis and Its Significant Effects on the Scavenging of Reactive Oxygen Radicals, *ACS Omega*, 2023, 8, 25, 22646-22655, incorporated herein by reference in its entirety]. All relevant equations, considering the assumptions and limitations mentioned in the references, have been adopted to calculate the oxygen vacancy concentration in $CeO_2$-based nanomaterials. The oxygen vacancy concentration (N; cm$^{-3}$) was calculated using the following equation (eq. 1)

$$N(\text{cm}^{-3}) = \frac{3}{4\pi L^3} \quad (1)$$

Where L represents the correlation length, which denotes the average distance between two lattice defects, and a signifies the radius of the $CeO_2$ molecule (0.34 nm). L is determined using the equation 2, where $d_g$ is the grain size of $CeO_2$.

$$L = \sqrt[3]{\left(\frac{\alpha}{2d_g}\right)^2 \left[(d_g - 2\alpha)^3 + 4d_g^2 \alpha\right]} \quad (2)$$

The grain size ($d_g$) of $CeO_2$ is calculated using equation 3, where Γ is the half-width at half-maximum (in cm$^{-1}$) derived from the peaks in various Raman spectra of the samples.

$$\Gamma = 5 + \frac{51.8}{d_g} \quad (3)$$

NH$_3$-temperature programmed desorption (TPD) and CO$_2$-TPD measurements were conducted using MICROTRAC-BELCAT II instrument with a thermal conductive detector (TCD). Catalysts (0.1 g) were pretreated at 600° C. (20° C./min) under a flow of helium for 30 min. Subsequently, the sample was treated with NH$_3$ or CO$_2$ at 100° C. for 30 min, and flushed with helium at this temperature for 15 min. The TPD experiment was conducted by increasing the temperature from room temperature to 700° C. at a rate of 10° C./min, while maintaining a flow of helium at 20 mL/min.

X-ray photoelectron spectroscopy (XPS) data were acquired using an ESCALab220i-XL electron spectrometer using 300 W Al Kα radiation. The samples were uniformly compressed into pellets with a thickness of 2 mm and subsequently affixed to a sample holder using double-sided adhesive tape. The binding energies were calibrated with reference to the adventitious C1s peak at 284.8 eV.

A 100 ml stainless steel reactor was used to perform the reactions. In the beginning, 100 mg of catalyst in the powder form was placed in the reactor. Next, 3.2 g (100 mmol) of methanol, and 5.2 g (50 mmol) of dehydrating reagent 2-Cyanopyridine were added into the reactor. To remove air from the reaction mixture, the reactor was purged 3 times with CO$_2$. Next, after pressurizing the reactor with 4 MPa of CO$_2$, the reaction mixture was stirred (500 rpm) and heated at 100° C. for 2 h. After completion of the reaction, the mixture was cooled down to room temperature and released the CO$_2$ pressure slowly. A quantitative amount of p-Xylene (1.23 mL; 10 mmol) was added to the mixture as an internal standard. Subsequently, after stirring for a few minutes, a part of this reaction mixture was filtered and analyzed by $^1$H NMR spectrometer (CDCl$_3$ solvent) to determine the yield and selectivity of DMC.

$$DMC \text{ yield} = \frac{DMC \text{ produced (mmol)}}{\text{Catalyst used }(g)} \quad (4)$$

$$DMC \text{ selectivity (\%)} = \frac{DMC \text{ produced (mmol)}}{DMC \text{ produced (mmol)} + (\text{byproducts (mmol)})} \times 100 \quad (5)$$

Assignment of $^1$H NMR peaks (600 MHz; CDCl$_3$; δ(ppm))

Internal standard (p-Xylene; C$_6$H$_4$(CH$_3$)$_2$): 2.30 ppm (s, 6H, C$_6$H$_4$(CH$_3$)$_2$), 7.06 ppm (s, 4H, C$_6$H$_4$(CH$_3$)$_2$). Methanol (CH$_3$OH): 3.46 ppm (s, 3H, CH$_3$OH). Dimethyl carbonate (CO(OCH$_3$)$_2$): 3.79 ppm (s, 6H, CO(OCH$_3$)$_2$). 2-Picolinamide (C$_5$H$_4$N(CONH$_2$)): 7.48-8.59 ppm (4 m, 4H, C$_5$H$_4$N (CONH$_2$)). 2-Cyanopyridine (C$_5$H$_4$N(CN)): 7.90-8.74 ppm (4 m, 4H, C$_5$H$_4$N(CN)). Methyl carbamate (CH$_3$O—CO—NH$_2$): 3.68 ppm (s, $^1$H, CH$_3$O—CO—NH$_2$), ~7.2 ppm (br, CH$_3$O—CO—NH$_2$)). Methyl picolinate (C$_5$H$_4$N (COOCH$_3$): 4.0 ppm (s, 3H, C$_5$H$_4$N(COOCH$_3$), 7.8-8.9 ppm (m, 4H, C$_5$H$_4$N(COOCH$_3$)).

Figure 2:
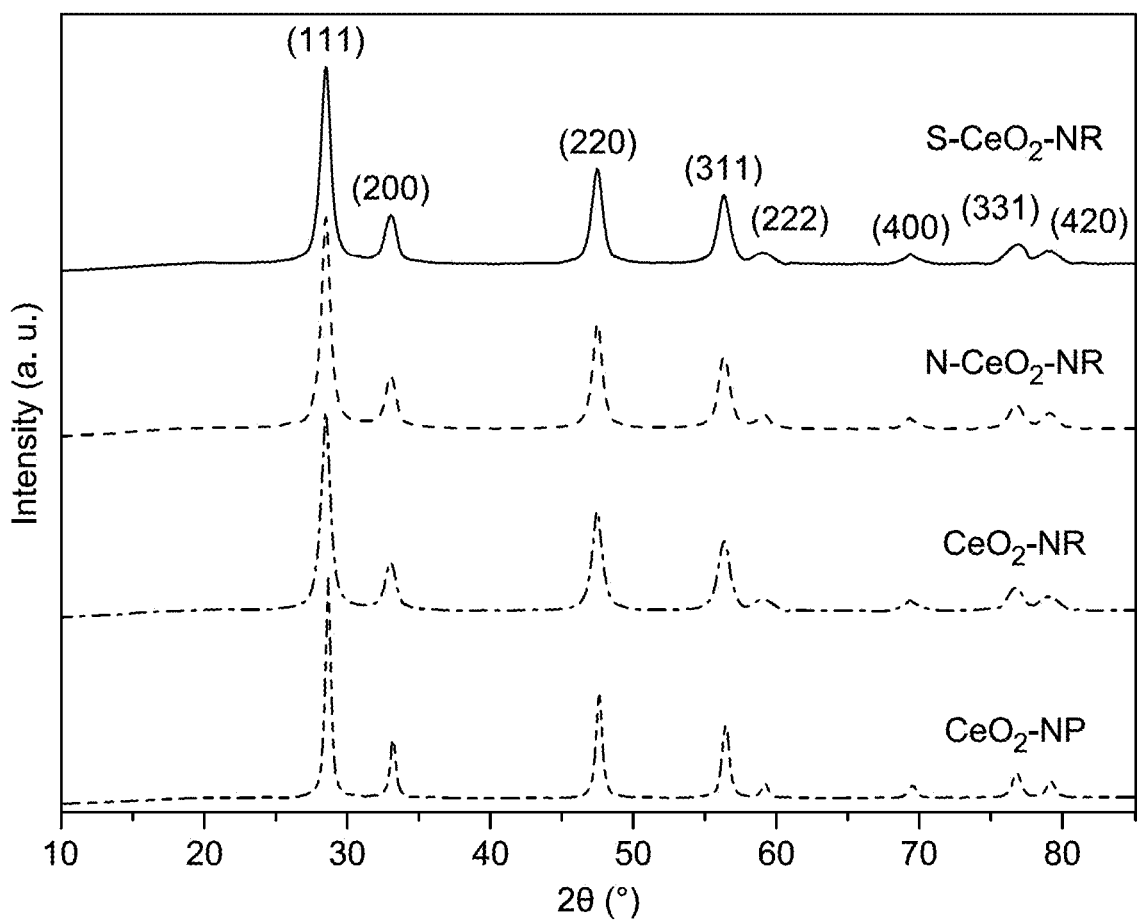
FIG. 2 is a powder X-Ray diffraction (PXRD) pattern of cerium dioxide nanoparticles ($CeO_2$-NP), cerium dioxide nanorods ($CeO_2$-NR), N-$CeO_2$-NR, and S-$CeO_2$-NR, according to certain embodiments.

The powder X-ray diffraction (PXRD) patterns (FIG. 2) of the CeO$_2$ nanorod catalysts (CeO$_2$-NR, N-CeO$_2$-NR, and S-CeO$_2$-NR) were investigated and compared with the commercial material CeO$_2$-NP (Sigma-Aldrich). The XRD analysis revealed diffraction peaks characteristic of a cubic fluorite structure with the space group Fm3m (JCPDS no. 34-0394). The nanorod catalysts displayed broader peaks compared to CeO$_2$-NP. This indicates that the nanorod materials exhibit smaller crystallite sizes (9.9-10.4 nm, Table 2) compared to CeO$_2$-NP (17.6 nm), as determined via Debye-Scherrer equation. These sizes were determined from the most intense peak corresponding to (111) crystal facet. Crystallite size for all the CeO$_2$ nanomaterials was calculated further based on (200), (220) and (311) crystal facets and are included in Table 3. The diffraction peaks at approximately 28.45°, 33.02°, 47.39°, 56.23°, 58.98°, 69.27°, 76.56°, and 78.90° were assigned to the (111), (200), (220), (311), (222), (400), (311), and (420) crystal facets of CeO$_2$ respectively. It has been reported that the lattice expansion is influenced by the reduction of Ce$^{4+}$ to Ce$^{3+}$ and the number of oxygen vacancies in CeO$_2$ nanomaterials. In this regard the lattice parameters were calculated and compared for N-CeO$_2$-NR, S-CeO$_2$- and pristine CeO$_2$-NR and CeO$_2$-NP. The lattice parameters (a) were calculated using the following formula (Eq. 6), where λ represents the wavelength of the light, θ represent the diffraction angle, d represent the interplanar spacing, and h, k, and l represent the Miller indices of the crystal planes.

$$a = \frac{n\lambda}{2\sin\theta}\sqrt{h^2 + k^2 + l^2} \quad (6)$$

The lattice parameters for N-CeO$_2$-NR, S-CeO$_2$-NR, CeO$_2$-NR and CeO$_2$-NP were estimated to be 5.433, 5.429 5.426 and 5.405 Å, respectively (refer to Table 2). The order of the gradual increase in the lattice parameter indicates a corresponding rise in Ce$^{3+}$ abundance and oxygen vacancies in the following sequence: CeO$_2$-NP<CeO$_2$-NR<S-CeO$_2$-NR<N-CeO$_2$-NR. Additionally, the absence of any peak in the PXRD pattern other than those associated with cerium-containing phases may represent the effective doping of the heteroatoms.

TABLE 2

Specific crystallite size, lattice parameters, interplanar spacing, surface area, pore volume, and Ce$^{3+}$ (%) of the CeO$_2$ nanomaterials, estimated from $^a$(111) plane of PXRD, $^b$N$_2$ physisorption and $^c$Ce 3d XPS analysis.

| Materials | 2θ (°)$^a$ | Crystallite size (nm)$^a$ | Lattice parameter (Å)$^a$ | Interplanar spacing (nm)$^a$ | Surface area (m$^2$/g)$^b$ | Pore volume (cm$^3$/g)$^b$ | Ce$^{3+}$ (%)$^c$ |
|---|---|---|---|---|---|---|---|
| CeO$_2$-NR | 28.458 | 10.4 | 5.426 | 0.313 | 85 | 0.405 | 17.8 |
| S-CeO$_2$-NR | 28.439 | 9.9 | 5.429 | 0.313 | 87 | 0.509 | 20.4 |
| N-CeO$_2$-NR | 28.421 | 10.1 | 5.433 | 0.313 | 86 | 0.648 | 21.8 |
| CeO$_2$-NP | 28.567 | 17.6 | 5.405 | 0.310 | 32 | 0.204 | 14.7 |

TABLE 3

Crystallite size measured from PXRD for
the $CeO_2$ nanomaterials, estimated from [a](111),
[b](200), [c](220) and [d](311) planes of PXRD analysis

| Materials | Crystalline Size (nm) | | | |
|---|---|---|---|---|
| | (111)[a] | (200)[b] | (220)[c] | (311)[d] |
| $CeO_2$-NR | 10.4 | 9.63 | 10.4 | 9.2 |
| S—$CeO_2$-NR | 9.9 | 9 | 9.5 | 8.9 |
| N—$CeO_2$-NR | 10.1 | 9.9 | 10.6 | 10 |
| $CeO_2$-NP | 17.6 | 18.9 | 17.8 | 17.4 |

Figure 3:
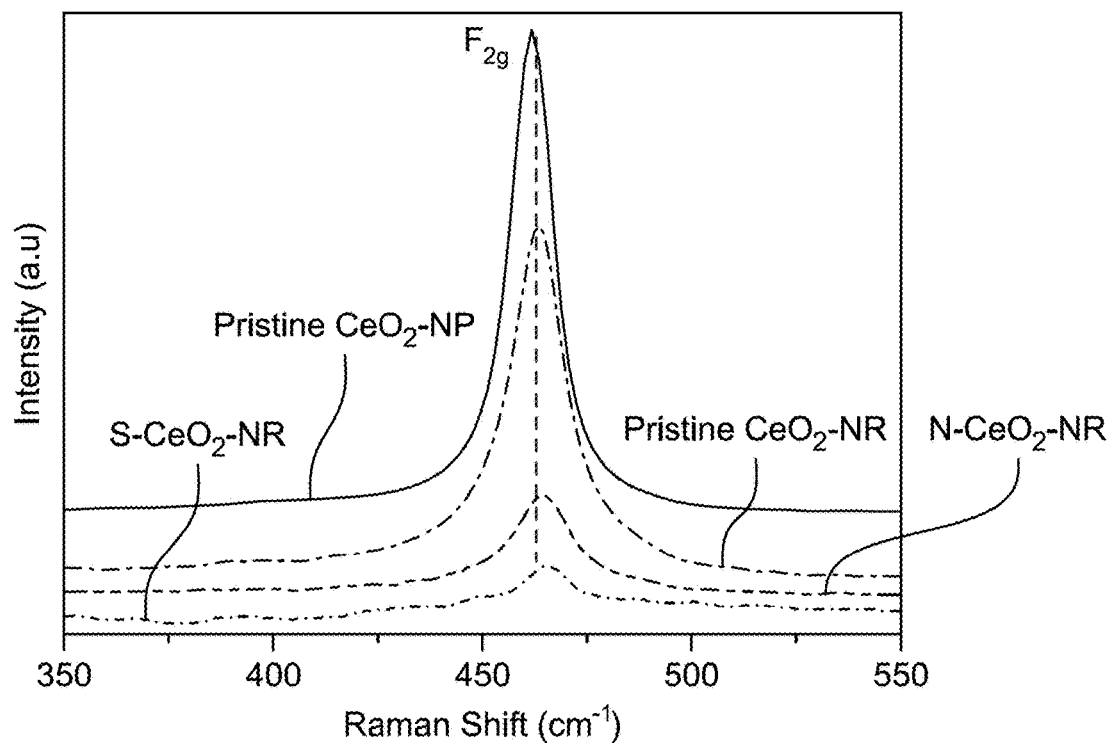
FIG. 3 is a Raman spectrum of pristine $CeO_2$-NP, pristine $CeO_2$-NR, N-$CeO_2$-NR and S-$CeO_2$-NR, according to certain embodiments.

The examination of surface oxygen vacancies on $CeO_2$-NR, X-$CeO_2$-NR and $CeO_2$-NP nanoparticles was carried out using Raman spectroscopy. This reveals that all the nanomaterials exhibited the characteristic Raman peak at approximately 462 cm$^{-1}$ (FIG. 3), associated with the symmetrical stretching ($F_{2g}$ mode) of Ce-O-Ce bonds. The N-$CeO_2$-NR and S-$CeO_2$-NR show a marginal blue shift of this stretching band. This shift may be attributed to crystal defects in the ceria lattice caused by implanted S and N atoms and a change in the lattice constant. Furthermore, a broadening and decrease in band intensity observed for these modified materials may imply enhanced oxygen vacancies in the materials. The surface oxygen vacancy concentrations in the samples were also determined by analyzing the degree of peak broadening. An alteration in oxygen vacancy concentration was observed for the X-$CeO_2$-NR materials in comparison to $CeO_2$-NR and $CeO_2$-NP (Table 4). Specifically, the sample N-$CeO_2$-NR exhibited the highest degree of oxygen vacancies (6.34×10$^{13}$ vacancies cm$^{-3}$) followed by S-$CeO_2$-NR (5.56×10$^{13}$ vacancies cm$^{-3}$), $CeO_2$-NR (4.59×10$^{13}$ vacancies cm$^{-3}$) and the commercial sample $CeO_2$-NP (1.51×10$^{13}$ vacancies cm$^{-3}$). Such improved oxygen vacancies in heteroatom-assisted nanomaterials were found to exhibit enhanced catalytic efficiency toward the synthesis of DMC involving $CO_2$ and methanol.

TABLE 4

Oxygen vacancy concentrations data

| Compound | Oxygen vacancy concentration (×10$^{13}$ vacancies cm$^{-3}$) |
|---|---|
| $CeO_2$-NP | 1.51 |
| $CeO_2$-NR | 4.59 |
| S—$CeO_2$-NR | 5.56 |
| N—$CeO_2$-NR | 6.34 |

Figure 4:
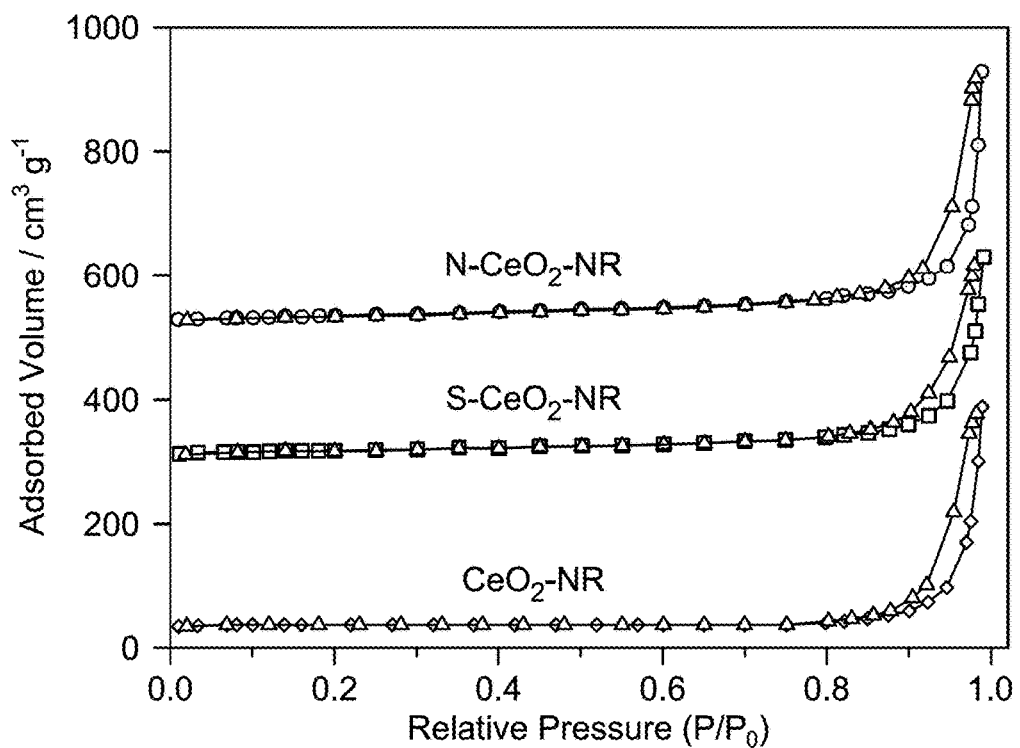
FIG. 4 is a graph depicting $N_2$ adsorption-desorption isotherms of $CeO_2$-NR, S-$CeO_2$-NR and N-$CeO_2$-NR, according to certain embodiments.
Figure 5:
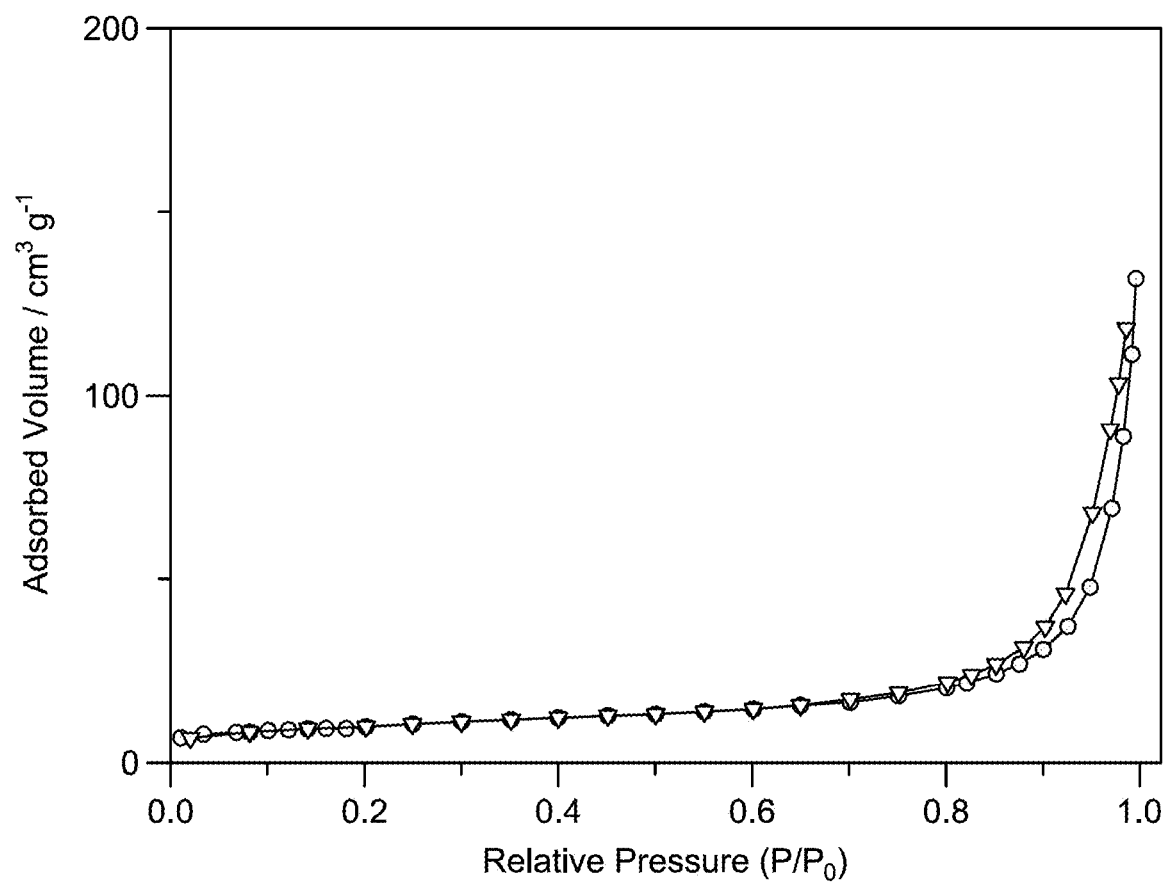
FIG. 5 is a graph depicting $N_2$ adsorption-desorption isotherm of $CeO_2$-NP, according to certain embodiments.
Figure 6A:
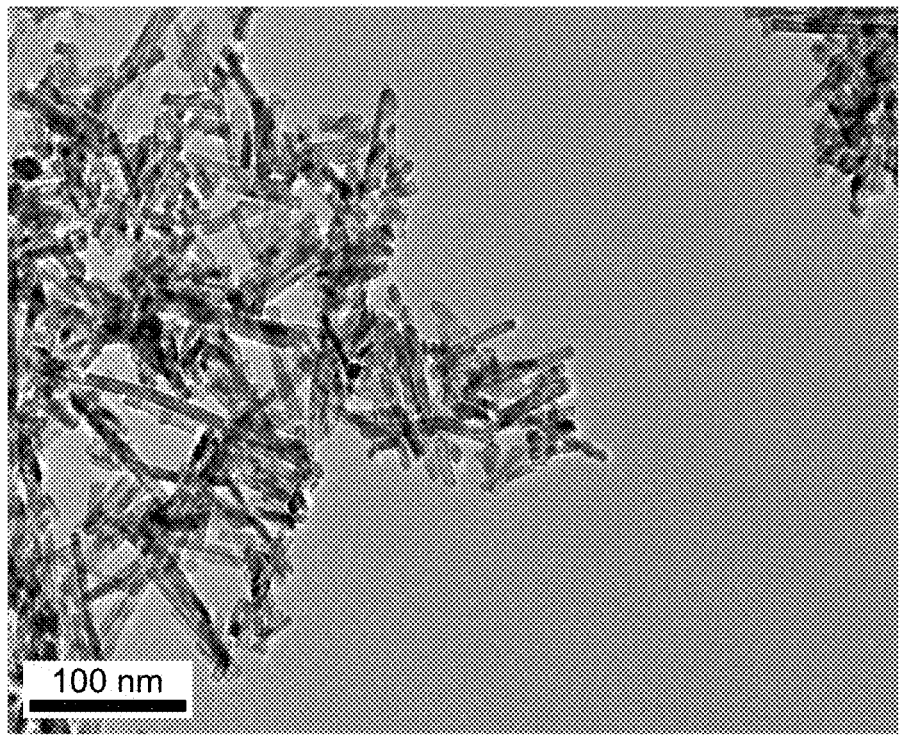
FIG. 6A is a transmission electron microscope (TEM) image of $CeO_2$-NR at 100 nm magnification, according to certain embodiments.
Figure 6B:
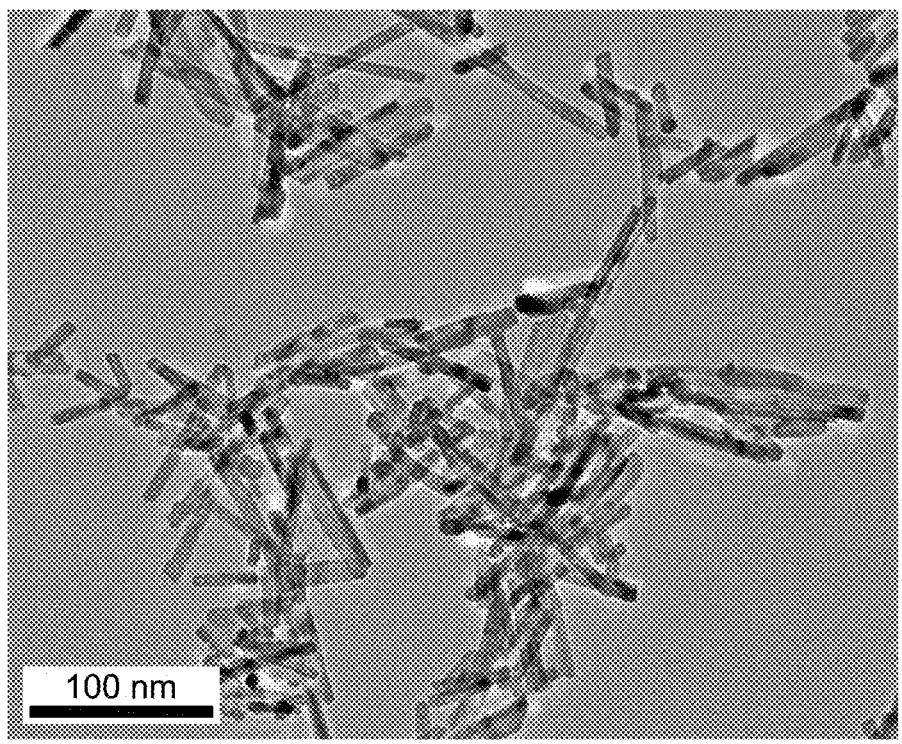
FIG. 6B is a TEM image of S-$CeO_2$-NR at 100 nm magnification, according to certain embodiments.
Figure 6C:
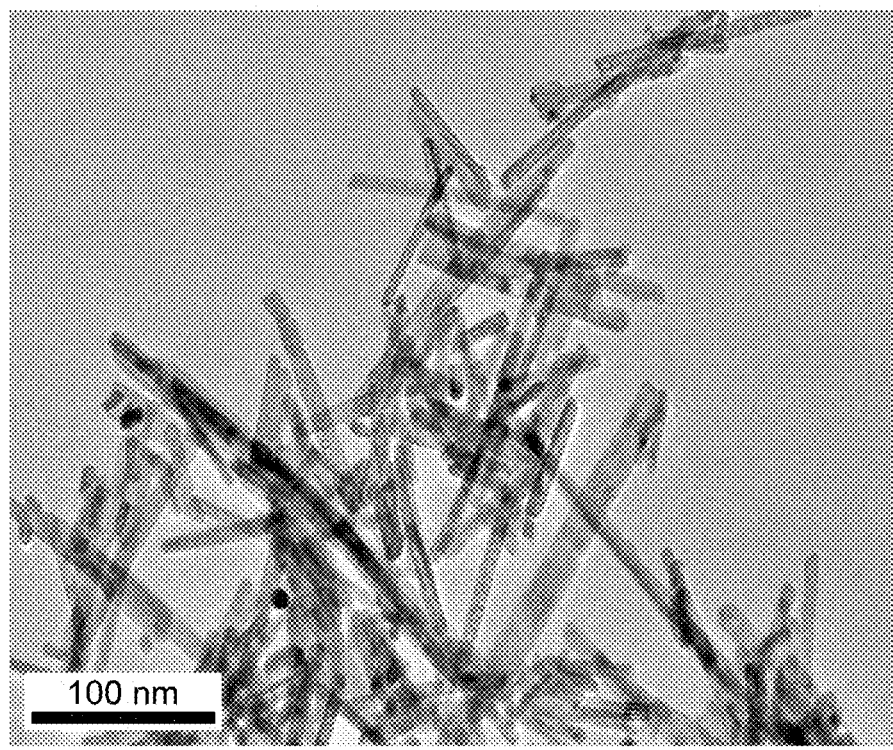
FIG. 6C is a TEM image of N-$CeO_2$-NR at 100 nm magnification, according to certain embodiments.
Figure 6D:
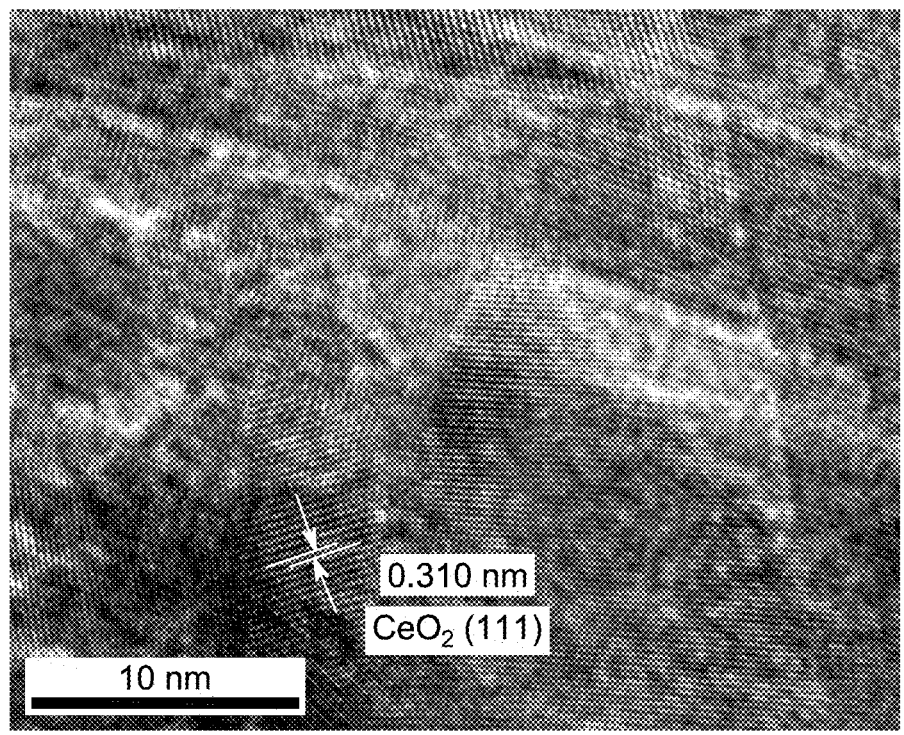
FIG. 6D is an image depicting the lattice spacing of $CeO_2$-NR at 10 nm magnification, according to certain embodiments.
Figure 6E:
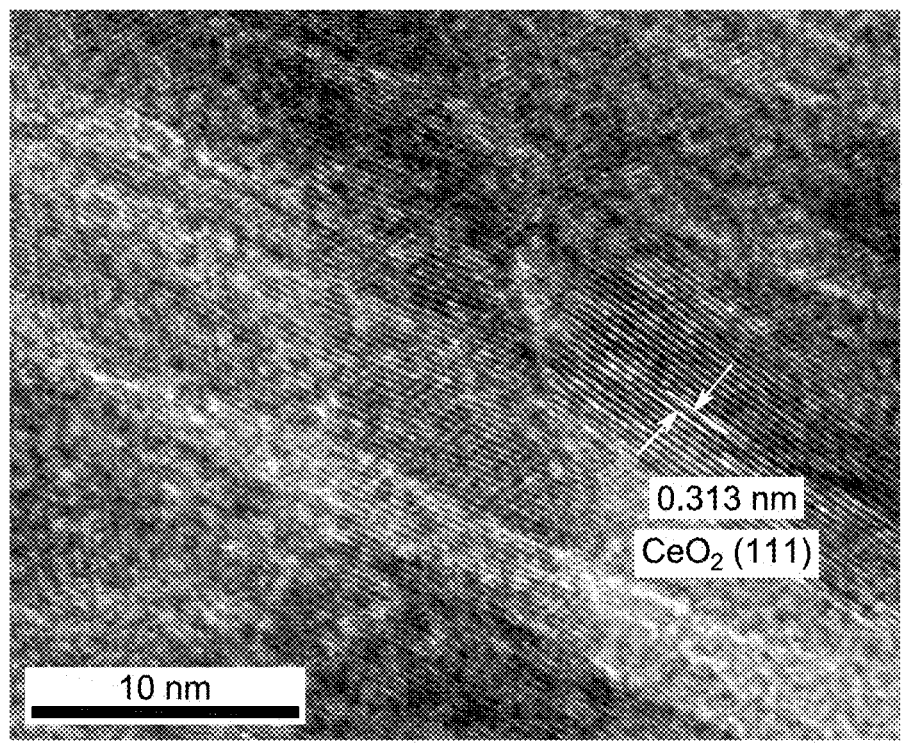
FIG. 6E is an image depicting the lattice spacing of S-$CeO_2$-NR at 10 nm magnification, according to certain embodiments.
Figure 6F:
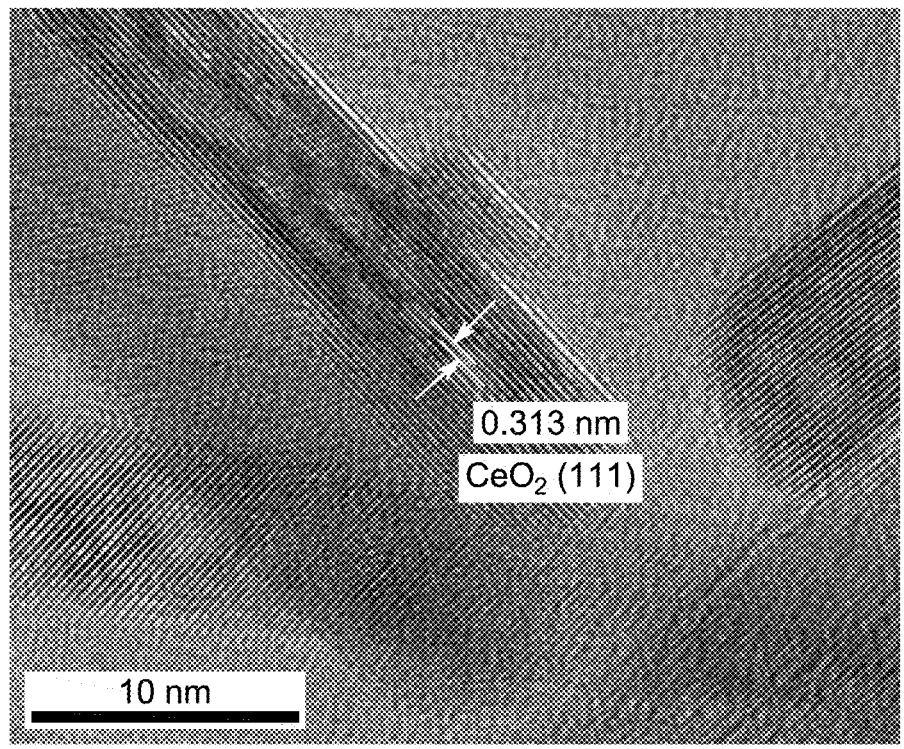
FIG. 6F is an image depicting the lattice spacing of N-$CeO_2$-NR at 10 nm magnification, according to certain embodiments.

The BET surface areas and pore volumes of the cerium oxide nanomaterials are detailed in Table 2. No substantial difference in surface area (85-87 m$^2$g$^{-1}$) was observed for the nanorod materials. Among the nanorod materials, the highest and lowest pore volumes were observed for N-$CeO_2$-NR (0.648 cm$^3$g$^{-1}$) and $CeO_2$-NR (0.405 cm$^3$g$^{-1}$), respectively. In contrast, the commercial $CeO_2$-NP demonstrated substantially lowest surface area (32.2 m$^2$g$^{-1}$) as well as pore volume (0.204 cm$^3$g$^{-1}$) in comparison to the synthesized nanorod materials. All the $CeO_2$ nanomaterials exhibited predominantly type IV isotherms (FIG. 4 and FIG. 5), aligning with previous reports. Notably, the N$_2$ adsorption-desorption plots show loops that could be interpreted either as type II or type IV isotherms. For example, in non-porous fumed silica, macroporous polymer-protein hybrid materials, or calcined metal-doped $CeO_2$ materials, capillary condensation is reported to occur at higher relative pressures, resulting in type II isotherms. However, $CeO_2$ nanomaterials, including $CeO_2$ nanorod materials, are most commonly interpreted to exhibit type IV isotherms including mesoporosity in the material.

Figure 7A:
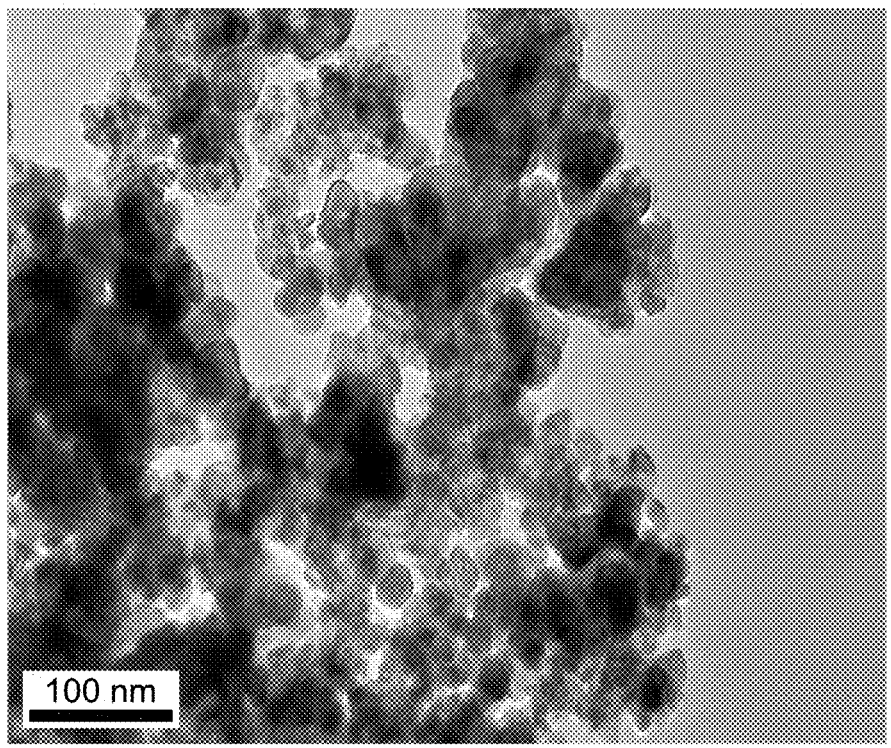
FIG. 7A is a TEM image of $CeO_2$-NP at 100 nm magnification, according to certain embodiments.
Figure 7B:
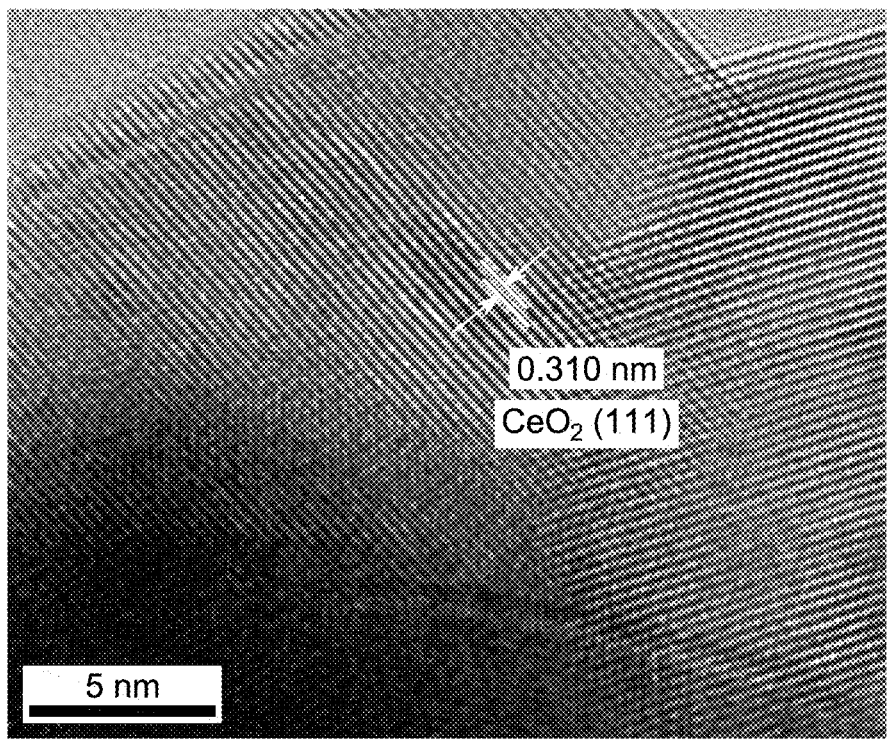
FIG. 7B is an image depicting the lattice spacing of $CeO_2$-NP at 5 nm magnification, according to certain embodiments.

The textural identity of the $CeO_2$ nanomaterials was investigated via TEM analysis (FIG. 6). The nanorod morphology of $CeO_2$-NR and X-$CeO_2$-NR were confirmed from the images (FIGS. 6A-6C). On the other hand, the commercial material $CeO_2$-NP exhibited a rather polyhedral type of appearance (FIG. 7). The high-resolution TEM images of $CeO_2$-NP, $CeO_2$-NR, and X-$CeO_2$-NR revealed lattice fringes with interplanar spacings in the range of 0.310-0.313 nm (FIG. 7 and FIGS. 6D-6F), corresponding to the (111) lattice planes of $CeO_2$ nanomaterials (JSPDS 34-0394). Furthermore, the interplanar spacings calculated from PXRD analysis for the (111) lattice plane closely match the HRTEM results (Table 2), confirming that the observed fringes correspond to the (111) lattice planes. It is also evident that there is a slight increase in lattice spacings for X-$CeO_2$-NR compared to pristine $CeO_2$-NP.

Figure 8A:
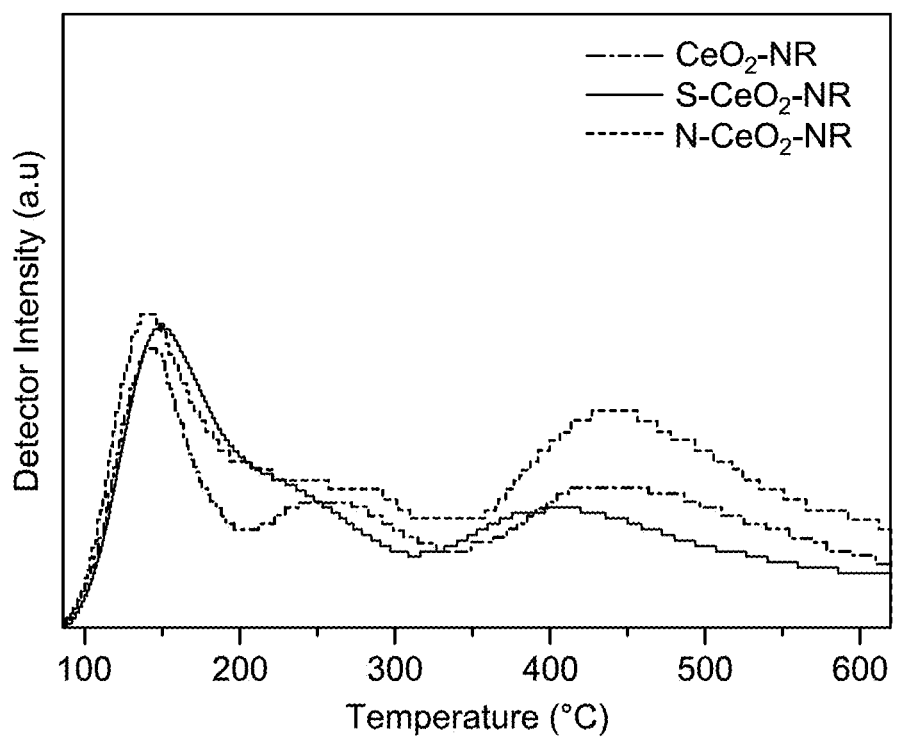
FIG. 8A is $CO_2$-temperature programmed desorption (TPD) profiles of $CeO_2$-NR, S-$CeO_2$-NR and N-$CeO_2$-NR, according to certain embodiments.
Figure 8B:
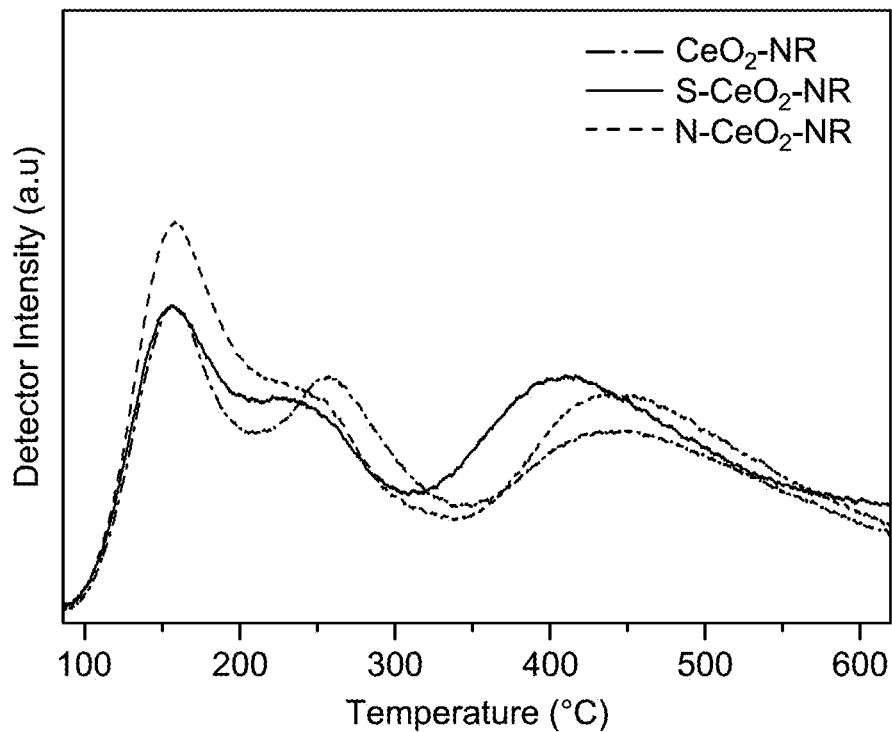
FIG. 8B is $NH_3$-TPD profiles of $CeO_2$-NR, S-$CeO_2$-NR and N-$CeO_2$-NR, according to certain embodiments.
Figure 9A:
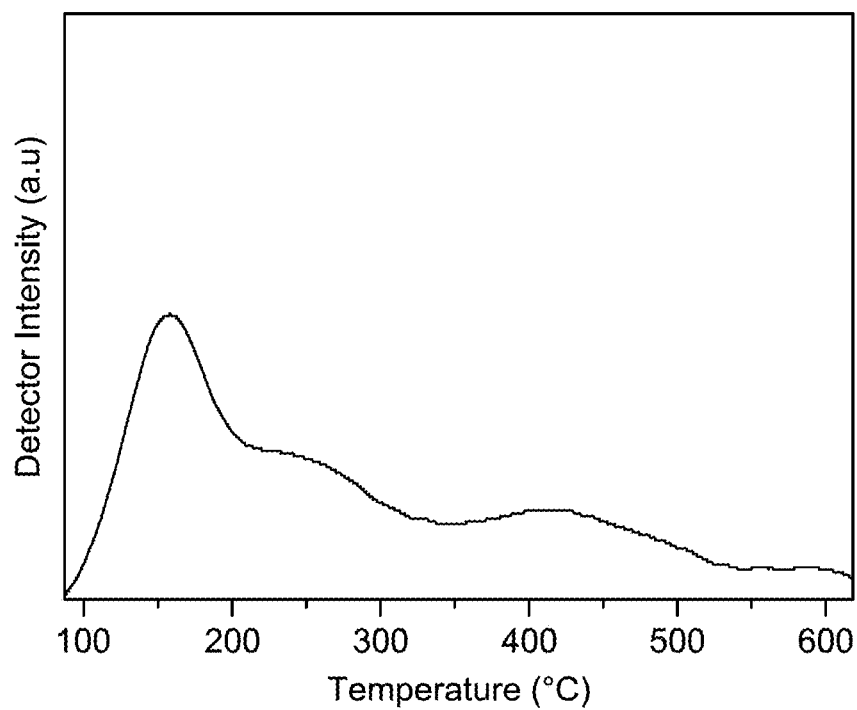
FIG. 9A is $CO_2$-TPD profiles of $CeO_2$-NP, according to certain embodiments.
Figure 9B:
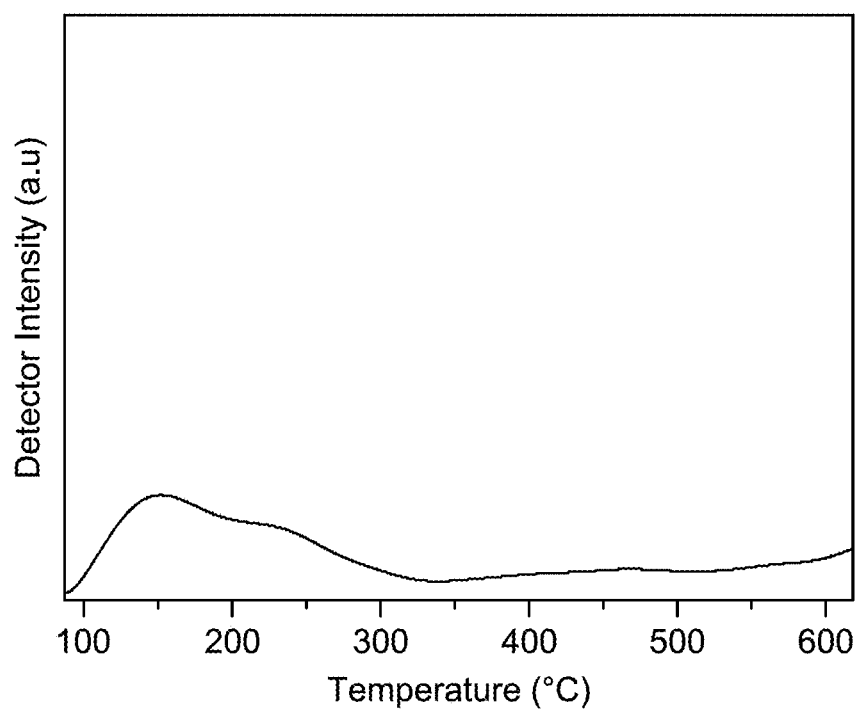
FIG. 9B is $NH_3$-TPD profiles of $CeO_2$-NP, according to certain embodiments.
Figure 10A:
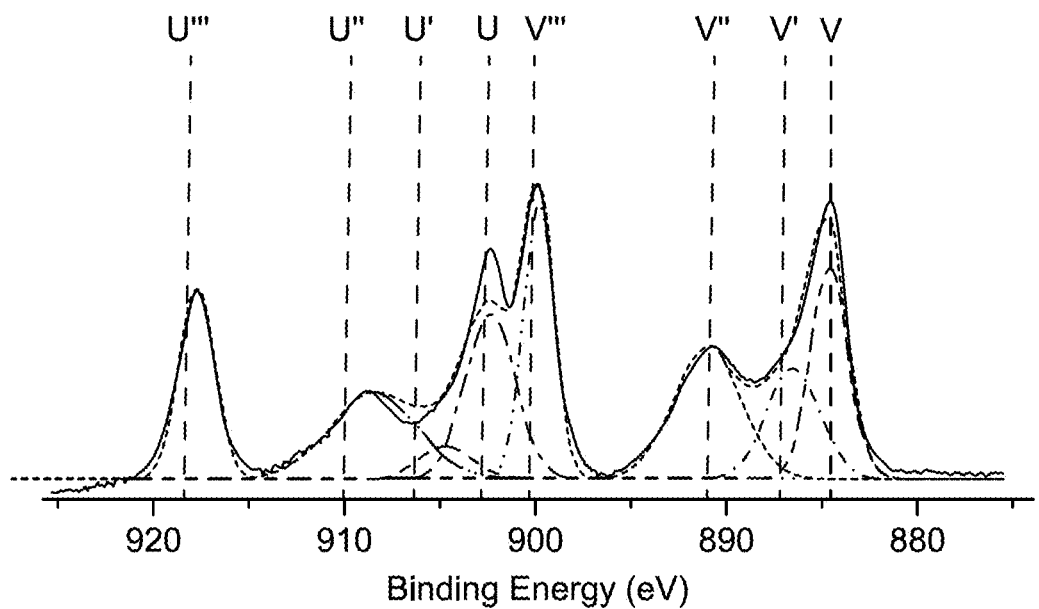
FIG. 10A is the Ce 3d X-ray Photoelectron Spectroscopy (XPS) spectrum of $CeO_2$-NP, according to certain embodiments.
Figure 10B:
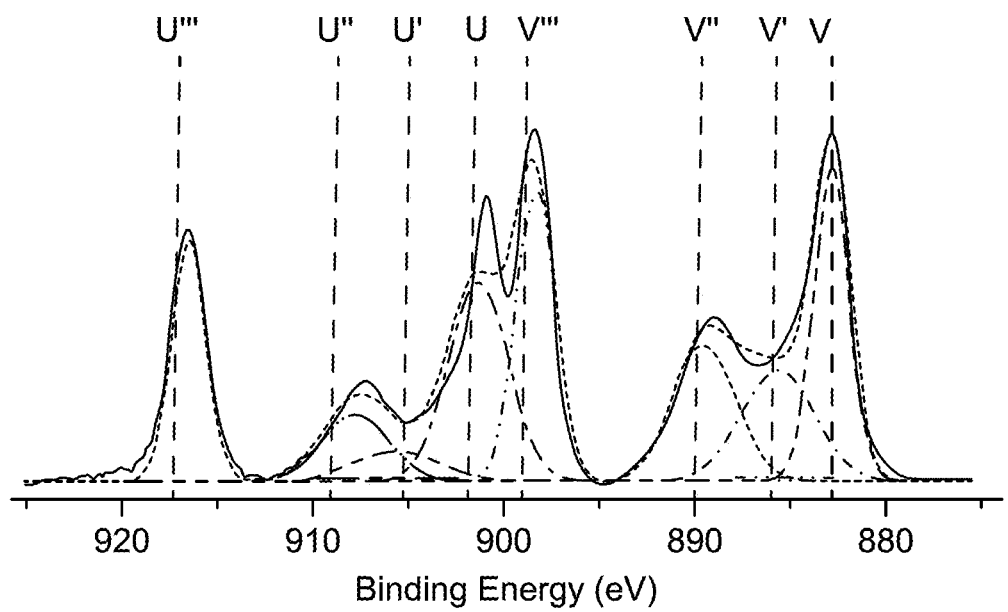
FIG. 10B is the Ce 3d XPS spectrum of $CeO_2$-NR, according to certain embodiments.
Figure 10C:
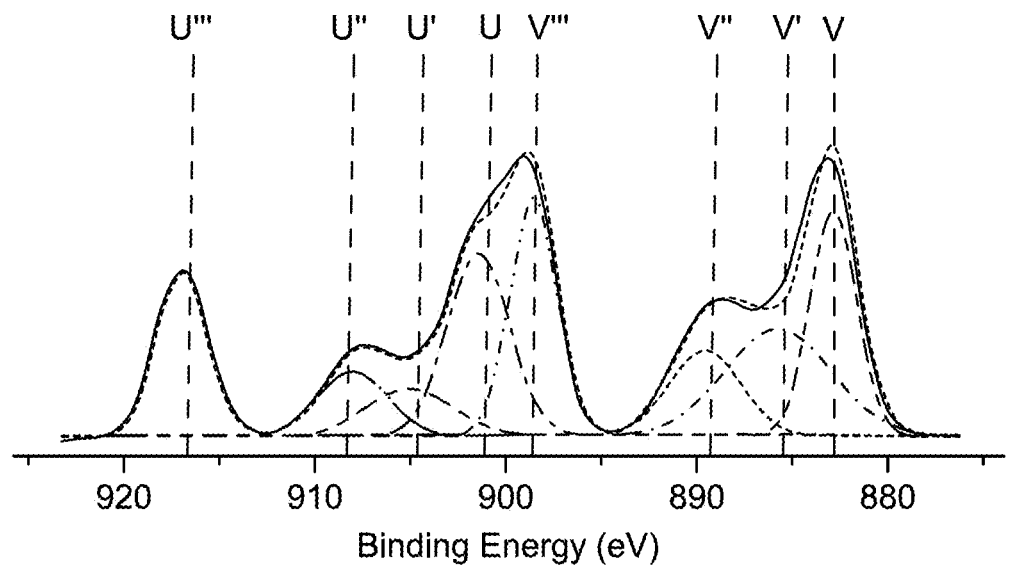
FIG. 10C is the Ce 3d XPS spectrum of S-$CeO_2$-NR, according to certain embodiments.
Figure 10D:
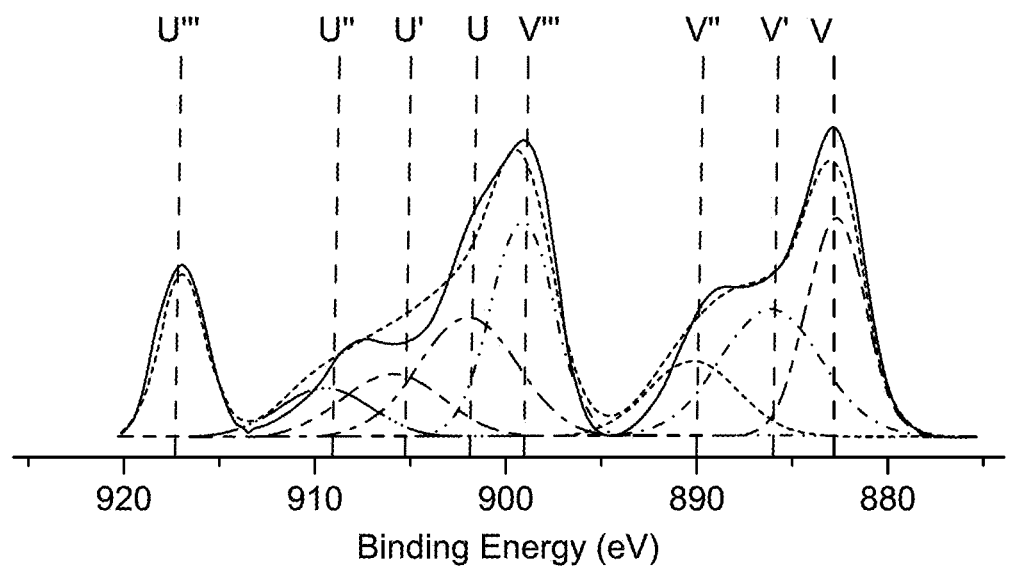
FIG. 10D is the Ce 3d XPS spectrum of N-$CeO_2$-NR, according to certain embodiments.
Figure 11A:
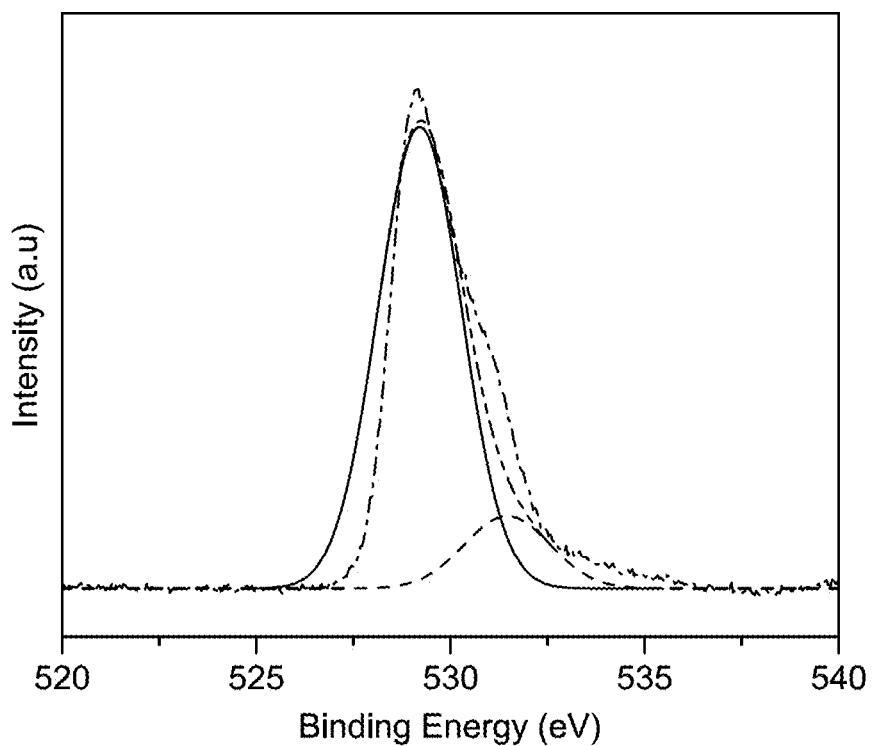
FIG. 11A is an O1s binding energy spectrum of $CeO_2$-NP, according to certain embodiments.
Figure 11B:
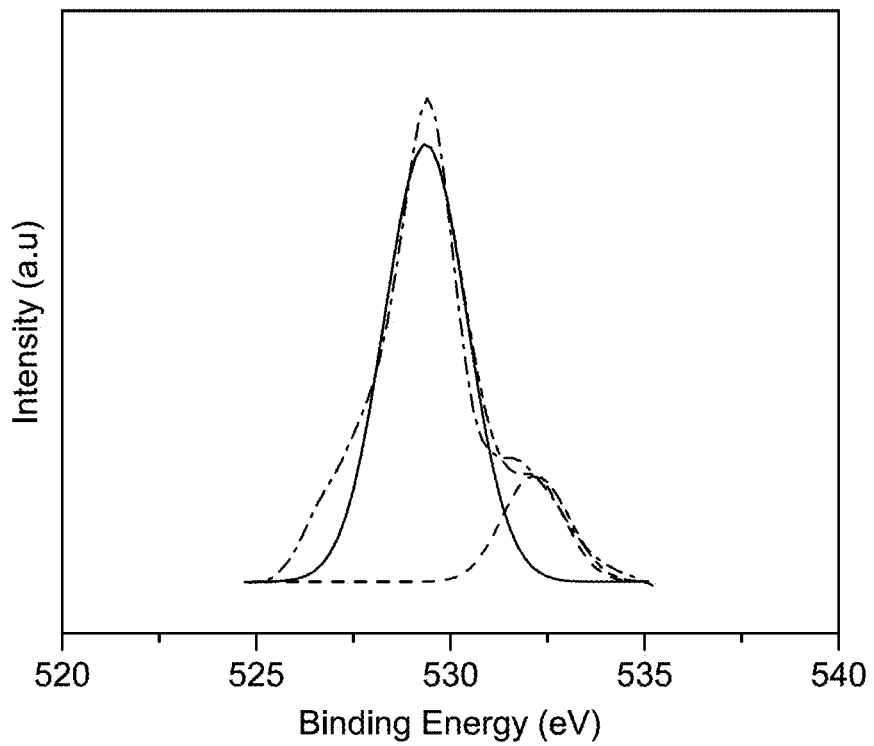
FIG. 11B is an O1s binding energy spectrum of $CeO_2$-NR, according to certain embodiments.
Figure 11C:
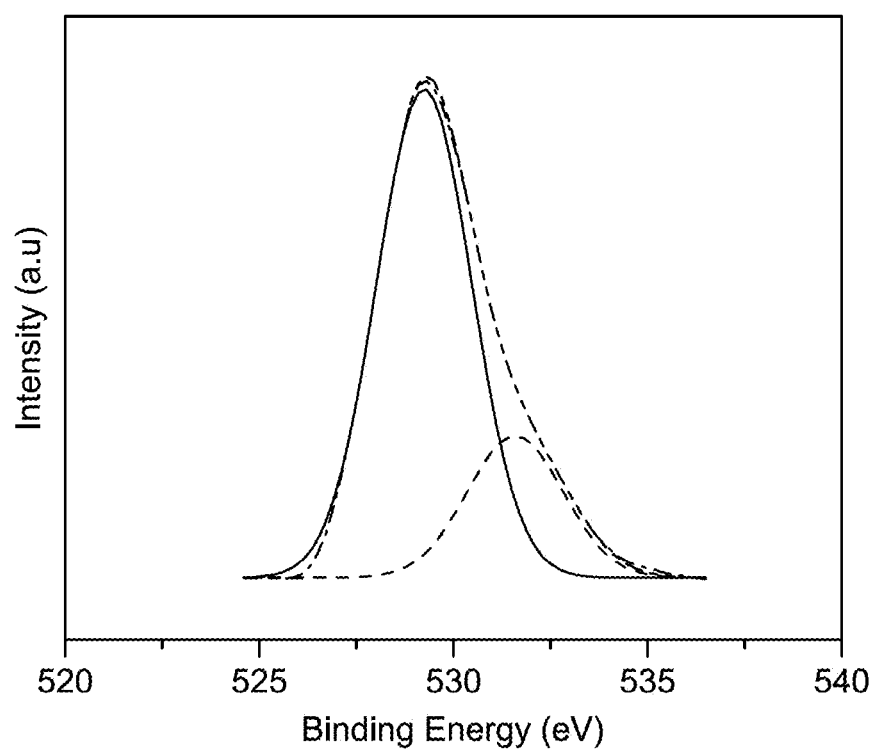
FIG. 11C is an O1s binding energy spectrum of S-$CeO_2$-NR, according to certain embodiments.
Figure 11D:
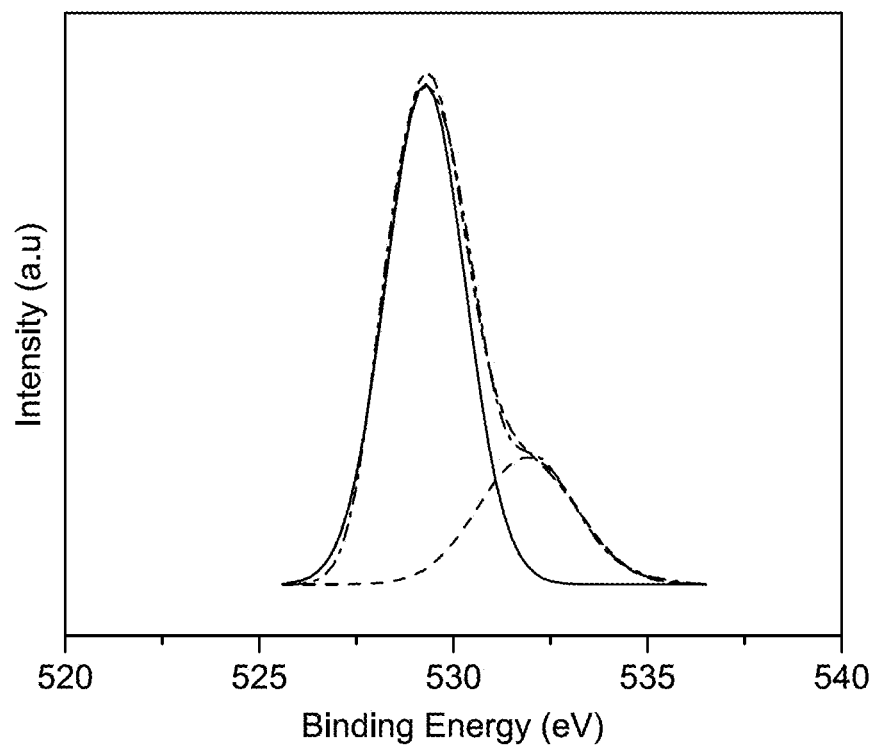
FIG. 11D is an O1s binding energy spectrum of N-$CeO_2$-NR, according to certain embodiments.

It is well-documented that $CeO_2$ materials exhibit acid-base bifunctional properties, consisting of both Lewis acidic and basic sites, specifically $Ce^{4+}$ and $O^{2-}$, respectively. While the basic sites activate $CO_2$, both basic and acidic sites are believed to be involved in activating methanol. To investigate the basic nature of the catalyst surface, $CO_2$-TPD was conducted and the results were plotted in FIG. 8A and FIG. 9A. Three distinctive desorption peak areas observed in temperatures below 200° C., between 20° and 350° C., and 350-600° C. signify the presence of weak, medium, and strong basic sites in the $CeO_2$ nanorod materials. From the $CO_2$ desorption data (Table 5) it is found that N-$CeO_2$-NR shows the highest surface basicity following the order N-$CeO_2$-NR>S-$CeO_2$-NR>$CeO_2$-NR>$CeO_2$-NP. Next, the surface acidity of the materials was explored through $NH_3$-TPD (FIG. 8B, FIG. 9B). The desorption plots also show 3 distinctive regions for the adsorption of $NH_3$ corresponding to weak (<200° C.), moderate (200-350° C.) and strong (350-600° C.) acid sites. The total acidity of N-$CeO_2$-NR was found to exceed the rest of $CeO_2$ nanomaterials. Such variation in the abundance of acid and base sites is anticipated to exhibit a difference in catalytic performance towards the synthesis of DMC from $CO_2$ and methanol.

TABLE 5

The basicity and acidity of the $CeO_2$ nanomaterials,
[a]Estimated from $CO_2$-TPD, [b]Estimated from $NH_3$-TPD.

| Materials | Surface basicity[a] (Adsorbed $CO_2$) (mmol/g) | Surface acidity[b] (Adsorbed $NH_3$) (mmol/g) |
|---|---|---|
| $CeO_2$-NR | 0.109 | 0.29 |
| S—$CeO_2$-NR | 0.113 | 0.298 |
| N—$CeO_2$-NR | 0.13 | 0.324 |
| $CeO_2$-NP | 0.099 | 0.048 |

The characteristics of CeO$_2$ nanomaterials were further investigated using XPS analysis. The assignment of peaks in the XPS spectrum of the Ce 3d lines of CeO$_2$ samples was conducted following the previous reports (FIG. 10).

Deconvolution of the Ce 3d spectra reveals eight distinct peaks: V (~882.5 eV), V' (~884.1 eV), V" (~888.4 eV), V'" (~898.0 eV), U (~899.8 eV), U' (~901.6 eV), U" (~907.5 eV), and U'" (~916.5 eV). The four U bands correspond to Ce 3d$_{3/2}$, while the four V bands represent Ce 3d$_{5/2}$. The 3d$^{10}$4f$^0$ state of the Ce$^{4+}$ species is denoted as peaks U, U", U'", V, V" and V'", whereas the 3d$^{10}$4f$^1$ state of the Ce$^{3+}$ is labelled as U' and V'. The surface concentration of Ce$^{3+}$ and Ce$^{4+}$ were determined utilizing the corresponding area of the bands.

$$C_e^{3+} = U' + V' \quad (7)$$

$$C_e^{4+} + U + U'' + U''' + V + V'' + V''' \quad (8)$$

$$[Ce^{3+}]\% = \left[\frac{A_{Ce^{3+}}}{A_{Ce^{3+}} + A_{Ce^{4+}}}\right] \times 100 \quad (9)$$

where $A_{Ce3+}$ represent the photoelectron peak areas of Ce$^{3+}$ and $A_{Ce4+}$ represents the photoelectron peak areas of Ce$^{4+}$.

The Ce$^{3+}$ % data tabulated in Table 2 demonstrated that Ce$^{3+}$ concentration follows the order of N-CeO$_2$-NR (21.8%)>S-CeO$_2$-NR (20.4%)>CeO$_2$-NR (17.8%)>CeO$_2$-NP (14.7%). Furthermore, the O1S binding energy spectra of these nanomaterials exhibit two deconvolution peaks at around 529.3 eV and 531.2 eV (FIG. 11). It has been well accepted that O1S peak for metal oxides is associated with a combination of oxygen species. The peak at in the region of 529.3 eV corresponds to the O$^{2-}$ species of O-Ce$^{4+}$ bond of lattice oxygen (OL), while the peak from 530.5-531.1 eV represents surface hydroxyl groups (—OH), and 531.1-532 eV could be attributed to the surface oxygen (Os) associated to O$^-$ species. Additionally, the band appears above 532.5 eV corresponds to adsorbed oxygen species including moisture. The surface oxygen (Os) is associated with O-Ce$^{3+}$ bond and oxygen vacancy. Therefore, the band extending from 530 to 535 eV consists of several oxygen species, as discussed above (FIG. 11). Hence, an exact estimation [%] of the Os species could not be determined. Overall, from NH$_3$- and CO$_2$-TPD, RAMAN, and XPS analyses it is evident that N-CeO$_2$-NR exhibited the highest level of surface acidity-basicity, oxygen vacancy, and Ce$^{3+}$ abundance (%).

Figure 12:
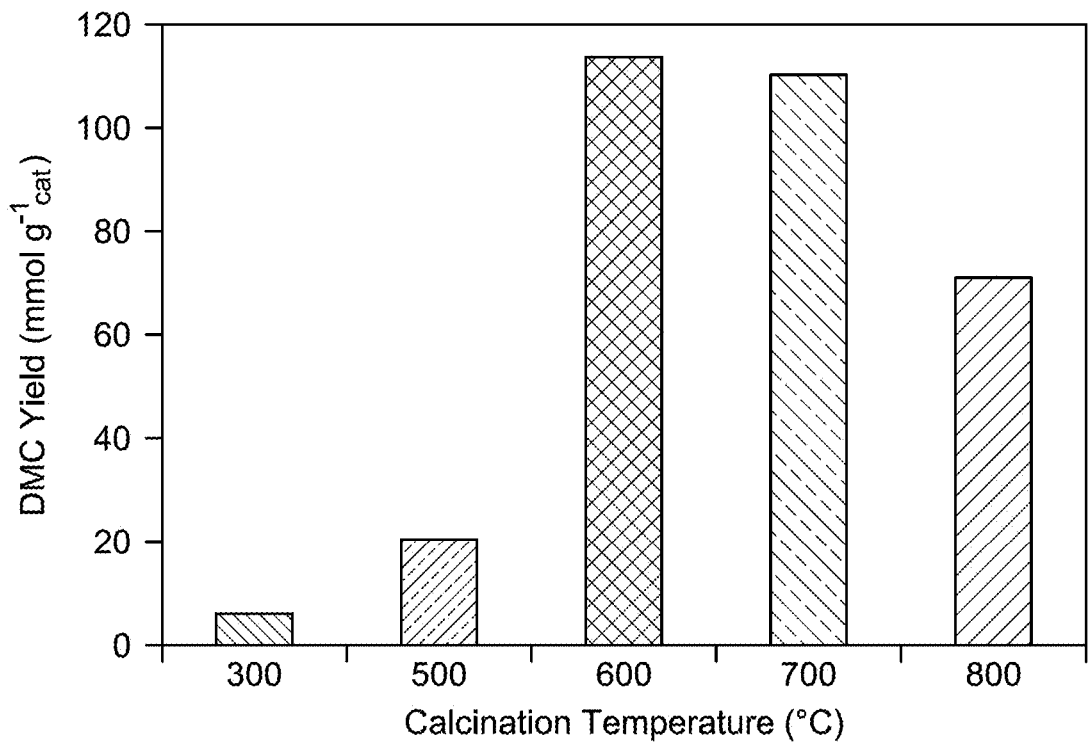
FIG. 12 is a bar graph depicting the effect of calcination temperature towards the efficiency of N-$CeO_2$-NR catalyst for DMC synthesis, according to certain embodiments.

The catalytic performance of CeO$_2$ materials (X-CeO$_2$-NR, CeO$_2$-NR and CeO$_2$-NP) was investigated for the synthesis of DMC from CO$_2$ and methanol in the presence of the dehydrating reagent 2-CP. Determination of the DMC yield (Table 6) revealed that the calcination temperature of CeO$_2$ materials plays a role in the efficacy of the catalysts (FIG. 12). A notable enhancement in yield was observed with an increase in calcination temperature from 300° C. to 600° C. This increase was highly pronounced for N-CeO$_2$-NR exhibiting a remarkable 19-fold rise in DMC yield. Subsequent elevations in calcination temperature led to a gradual decrease in catalytic activity. Based on these observations all the nanomaterials were subjected to calcination at 600° C. before employing in catalytic reaction.

TABLE 6

Effect of calcination temperature on the performances of X-CeO$_2$-NR catalysts.
Reaction conditions: 100 mg catalyst, Methanol (3.20 g, 100 mmol), 2-cyanopyridine (2-CP: 5.20 g, 50 mmol), CO$_2$ (4 MPa), 100° C., 2 h. The DMC yield and selectivity were estimated using $^1$H NMR spectra.

| Entry | Catalysts | Calcination temp. (° C.) | Dehydrating reagent | MeOH conversion (%) | DMC yield (mmol g$_{cat}^{-1}$) | DMC | Selectivity (%) Methyl picolinate | Methyl carbamate |
|---|---|---|---|---|---|---|---|---|
| 1 | N-CeO$_2$-NR | 300 | 2-CP | 1.2 | 5.7 | 100 | 0 | 0 |
| 2 | N-CeO$_2$-NR | 500 | 2-CP | 4.1 | 20.3 | 100 | 0 | 0 |
| 3 | N-CeO$_2$-NR | 600 | 2-CP | 22.7 | 113.3 | 100 | 0 | 0 |
| 4 | N-CeO$_2$-NR | 700 | 2-CP | 22.0 | 110.0 | 100 | 0 | 0 |
| 5 | N-CeO$_2$-NR | 800 | 2-CP | 14.3 | 70.7 | 100 | 0 | 0 |
| 6 | S-CeO$_2$-NR | 300 | 2-CP | 1.1 | 5.3 | 100 | 0 | 0 |
| 7 | S-CeO$_2$-NR | 600 | 2-CP | 9.9 | 49.7 | 100 | 0 | 0 |

Moreover, it was observed that the yield of DMC also strongly correlated with the $CO_2$ pressure and a stoichiometric amount of 2-CP as evidenced from the data in Table 7. A decrease in $CO_2$ pressure was found to reduce the DMC yield. Most notably, the catalyst N-CeO$_2$-NR exhibited a high DMC yield (55.2 mmol $g_{cat}^{-1}$) even at a low $CO_2$ pressure of 0.4 MPa. Conversely, when the reaction was conducted at atmospheric $CO_2$ pressure (0.1 MPa), the DMC yield reduced drastically (0.8 mmol $g_{cat}^{-1}$). This implies that achieving high catalytic efficiency requires a substantial $CO_2$ pressure in the reactor system. Moreover, an increase in the amount of 2-CP from half equivalent (entry 1, Table 7) to one equivalent (entry 2, Table 7) with respect to methanol reduced the yield of DMC from 113.3 mmol $g_{cat}^{-1}$ to 74.5 mmol $g_{cat}^{-1}$. Such lowering in catalytic efficiency may indicate the blocking of active $CeO_2$ sites by excess of 2-CP. Notably, the absence of the dehydrating reagent (2-CP) in the reaction mixture led to a drastic dropping in the yield of DMC to 4.7 mmol $g_{cat}^{-1}$ (entry 5, Table 7).

TABLE 7

Effect of $CO_2$ pressure and 2-CP on the performances of N-CeO$_2$-NR catalyst towards DMC yield.

| Entry | $CO_2$ (MPa) | Dehydrating reagent | MeOH conversion (%) | DMC yield (mmol $g_{cat}^{-1}$) | DMC | Selectivity (%) Methyl picolinate | Methyl carbamate |
|---|---|---|---|---|---|---|---|
| 1[a] | 4 | 2-CP | 22.7 | 113.3 | 100 | 0 | 0 |
| 2[a] | 0.4 | 2-CP | 11 | 55.2 | 100 | 0 | 0 |
| 3[a] | 0.1 | 2-CP | 0.2 | 0.8 | 100 | 0 | 0 |
| 4[b] | 4 | 2-CP | 14.9 | 74.5 | 100 | 0 | 0 |
| 5 | 4 | — | 1 | 4.7 | 100 | 0 | 0 |

Reaction conditions: 100 mg catalyst, Methanol (3.20 g, 100 mmol), $CO_2$ (4 MPa), 100° C., 2 h. The DMC yield and selectivity were estimated using $^1$H NMR spectra. [a]2-cyanopyridine (2-CP: 5.20 g, 50 mmol), [b]2-cyanopyridine (2-CP: 10.4 g, 100 mmol).

Figure 13:
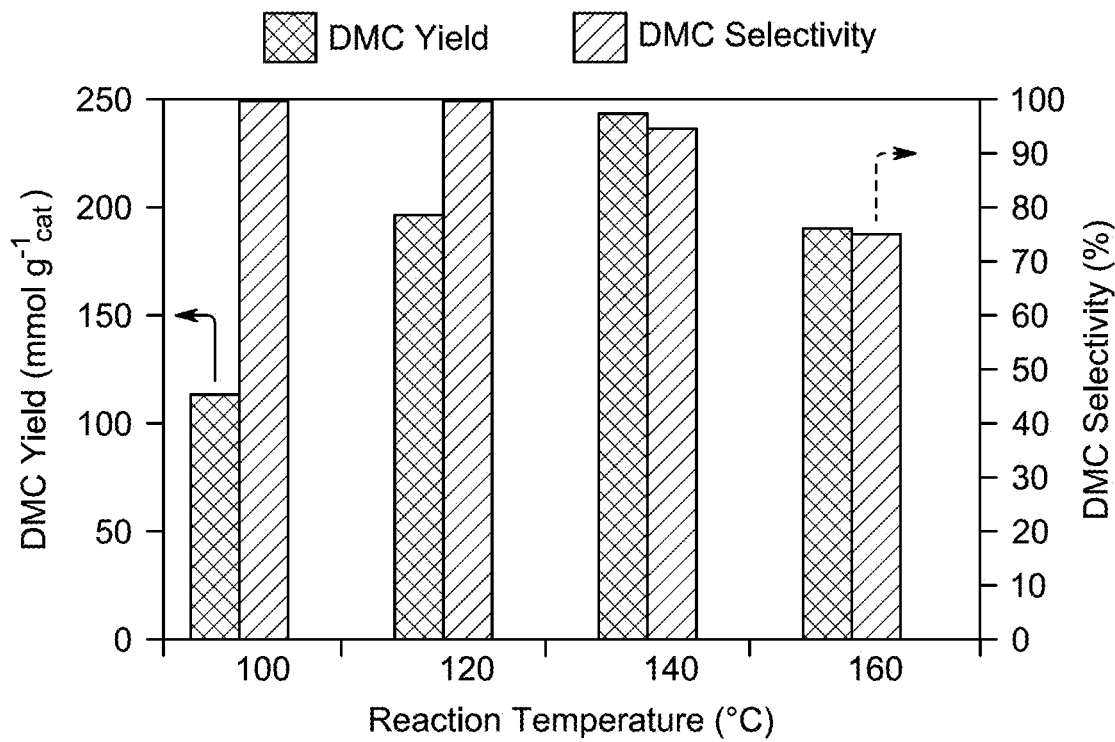
FIG. 13 is a bar graph depicting reaction temperature vs DMC yield and DMC selectivity (%) plots for the catalytic performance of N-$CeO_2$-NR, according to certain embodiments.
Figure 14A:
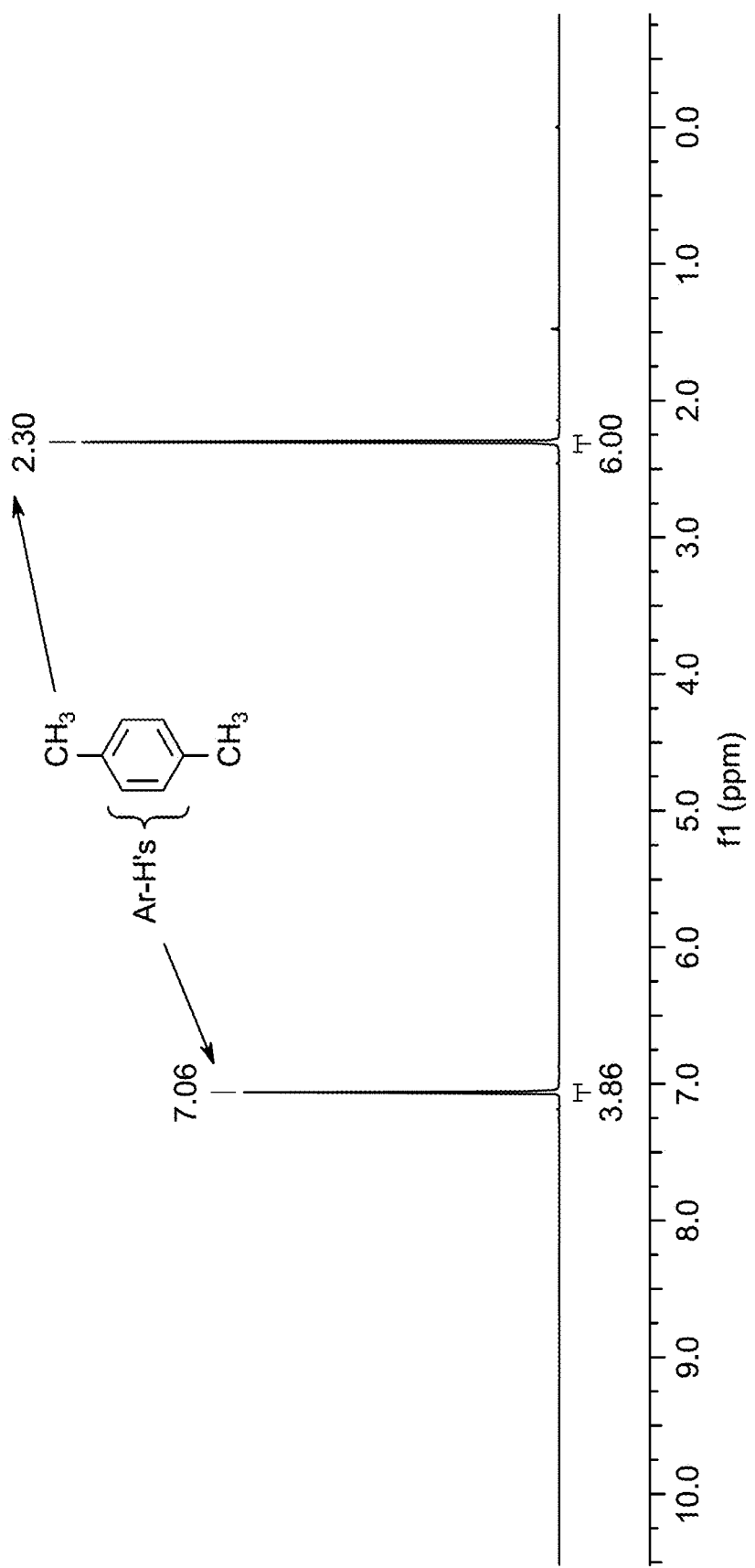
FIG. 14A is proton nuclear magnetic resonance ($^1H$ NMR) spectrum of p-Xylene, according to certain embodiments.
Figure 14B:
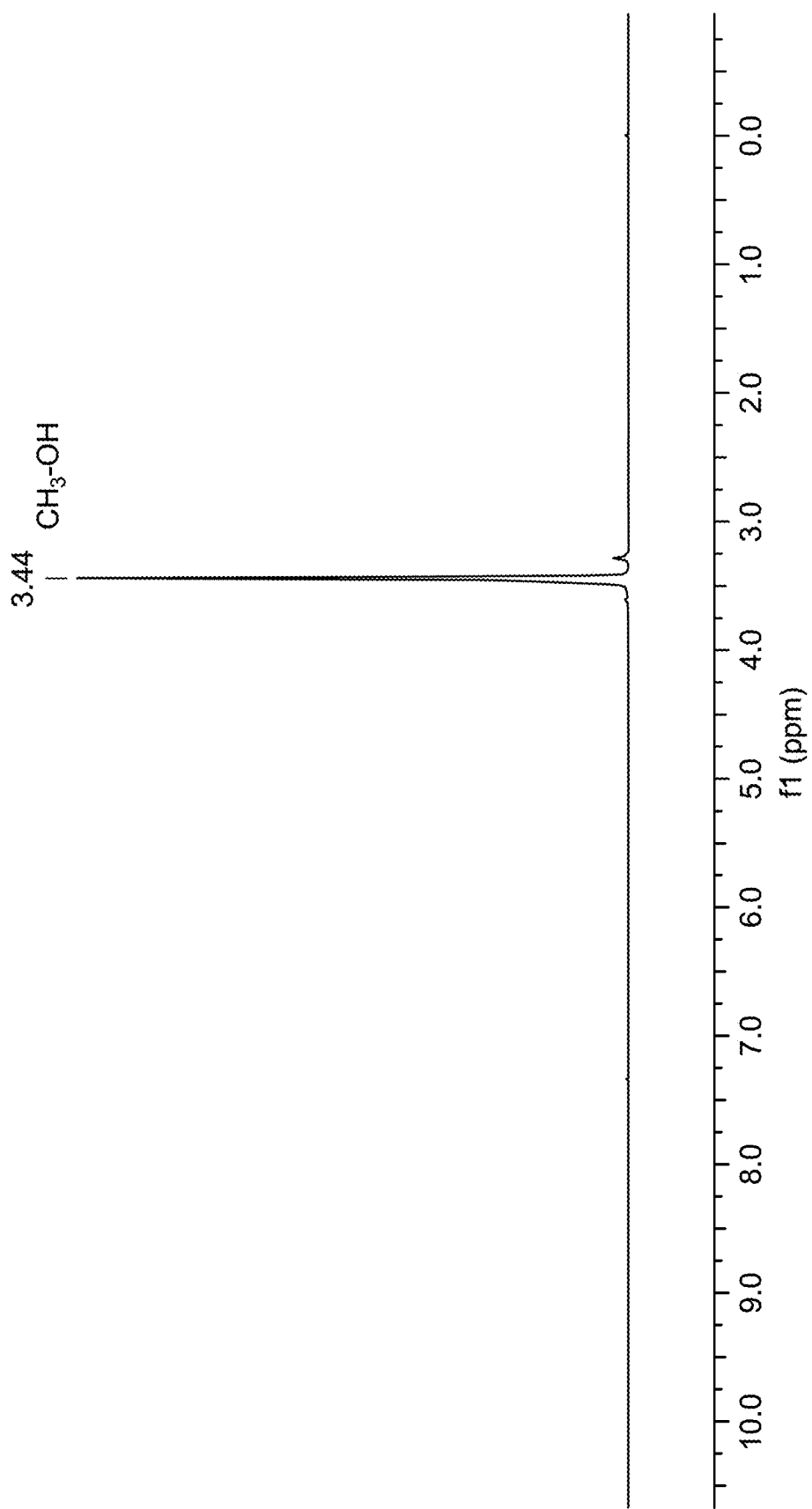
FIG. 14B is $^1H$ NMR spectra of methanol, according to certain embodiments.
Figure 14C:
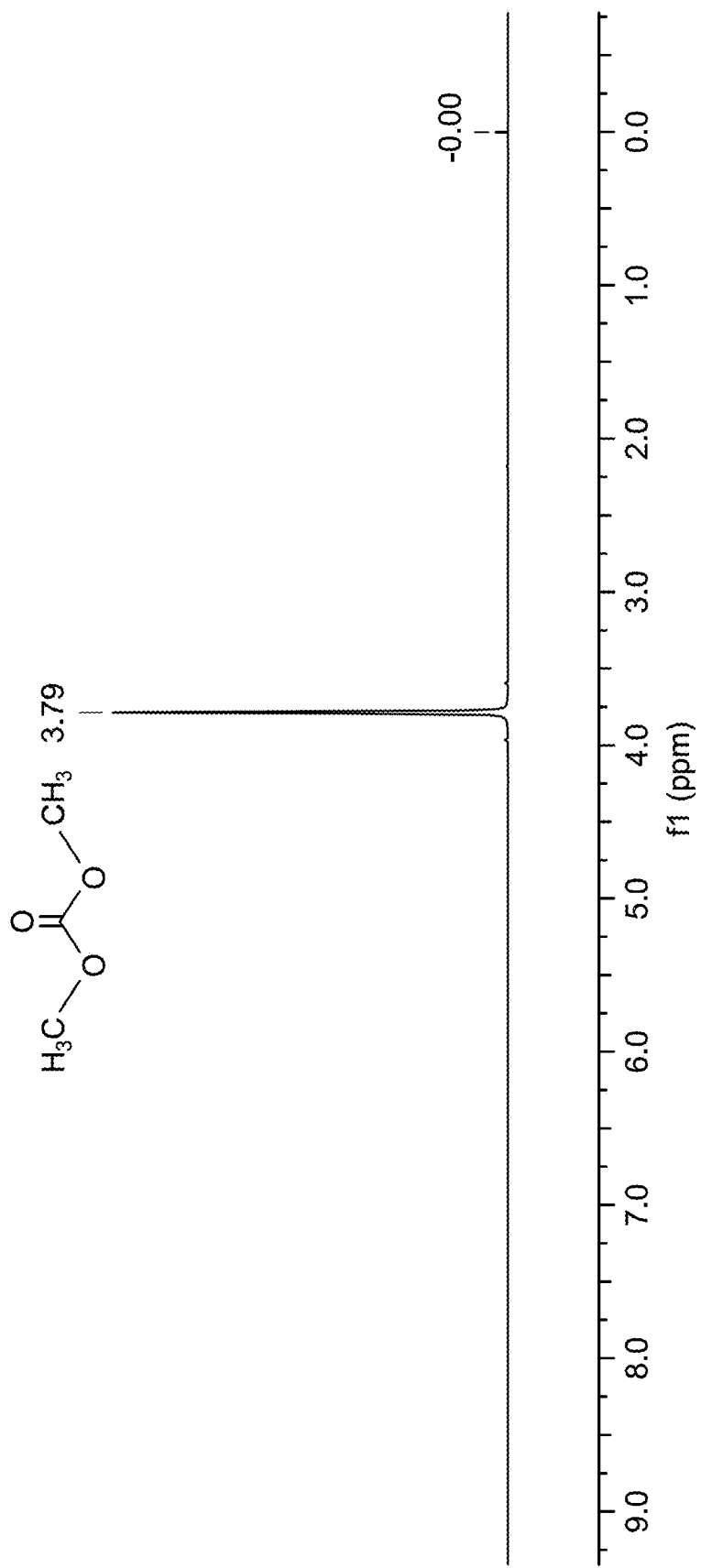
FIG. 14C is $^1H$ NMR spectra of dimethyl carbonate, according to certain embodiments.
Figure 14D:
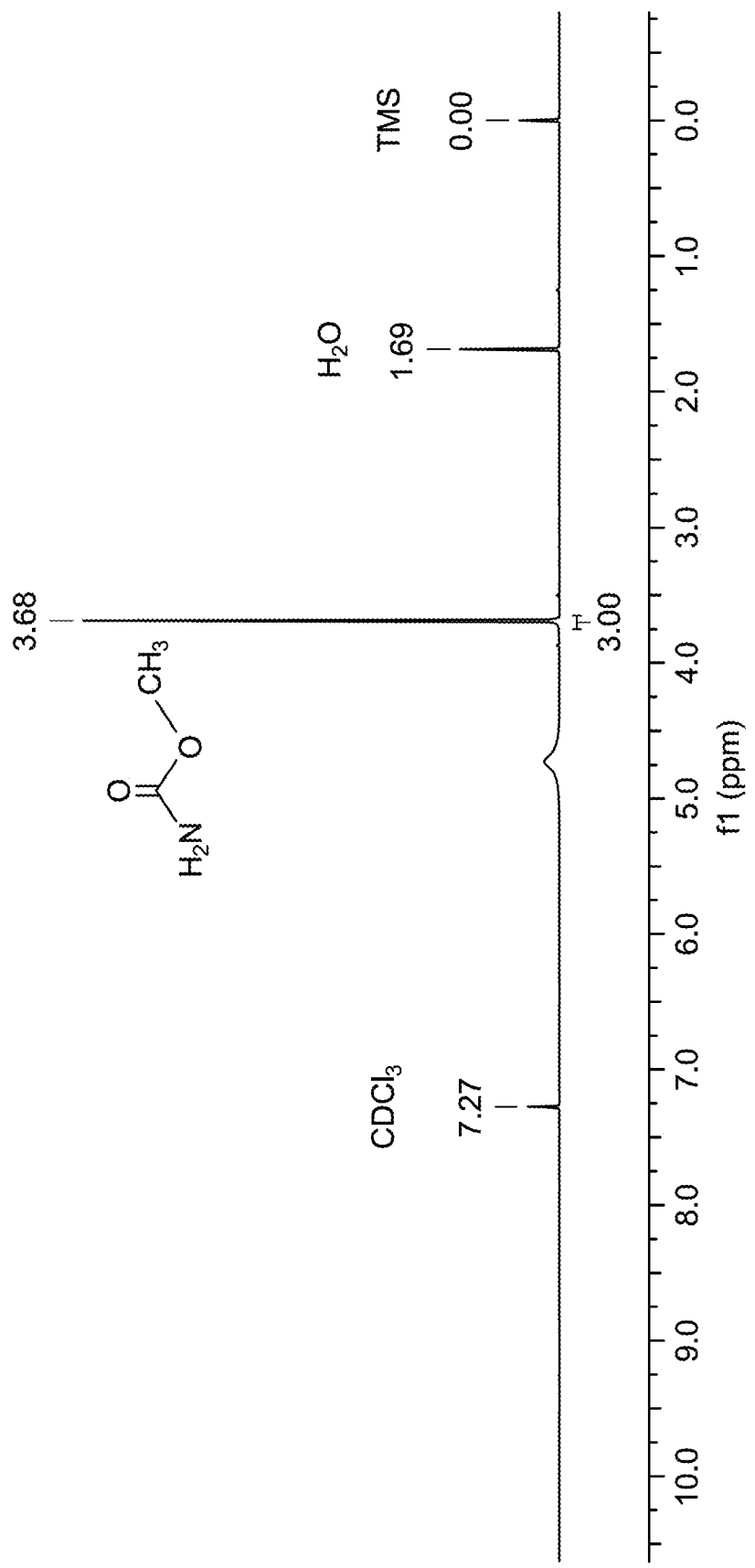
FIG. 14D is $^1H$ NMR spectra of methyl carbamate, according to certain embodiments.
Figure 14E:
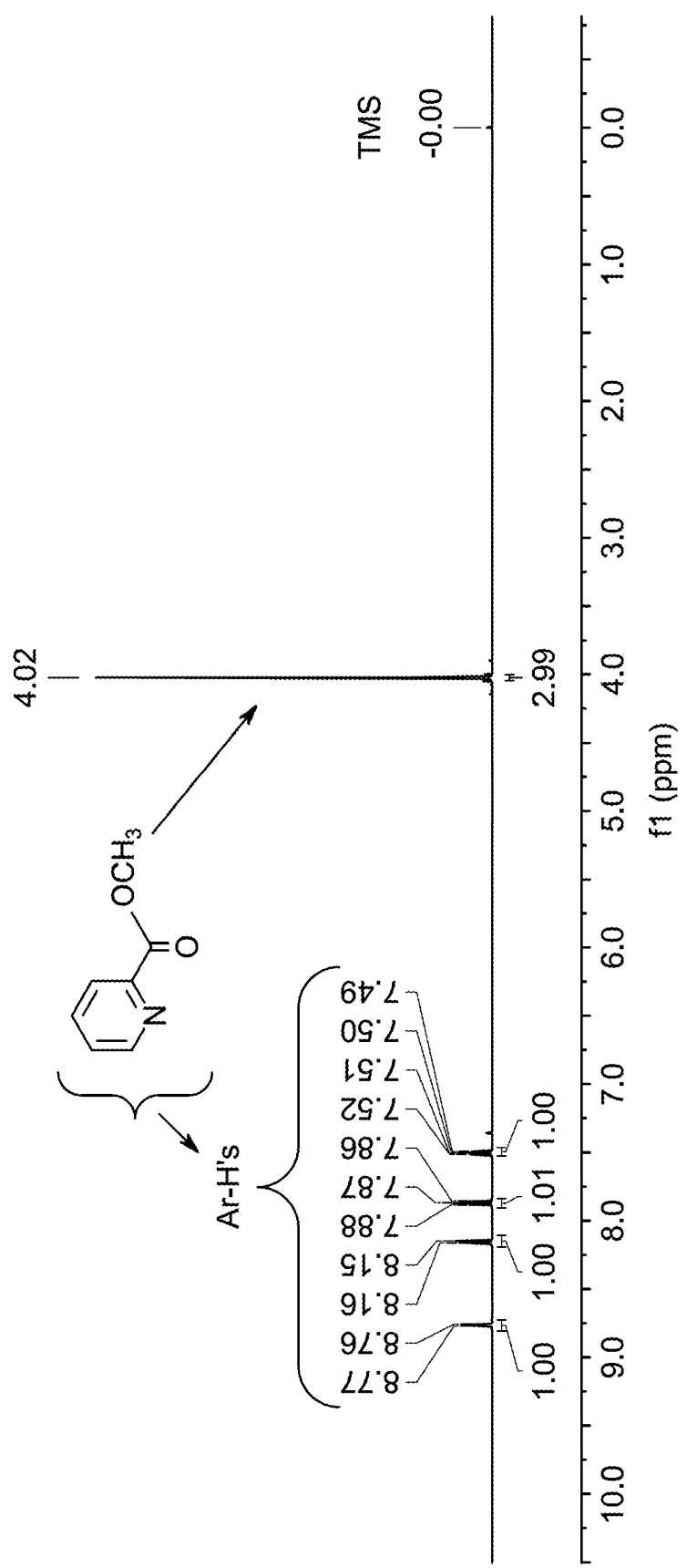
FIG. 14E is $^1H$ NMR spectra of methyl picolinate, according to certain embodiments.
Figure 14F:
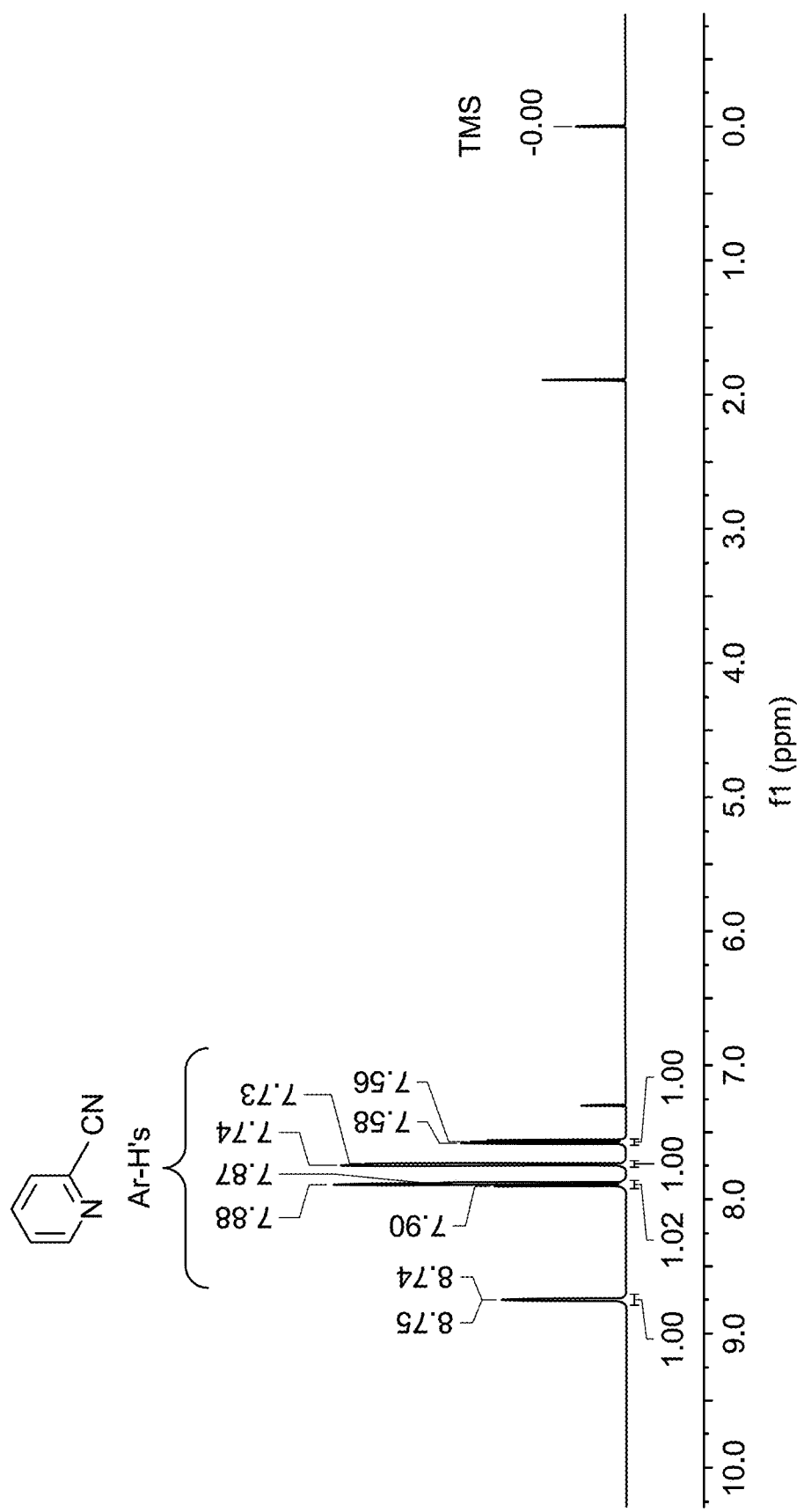
FIG. 14F is $^1H$ NMR spectra of 2-cyano pyridine, according to certain embodiments.
Figure 14G:
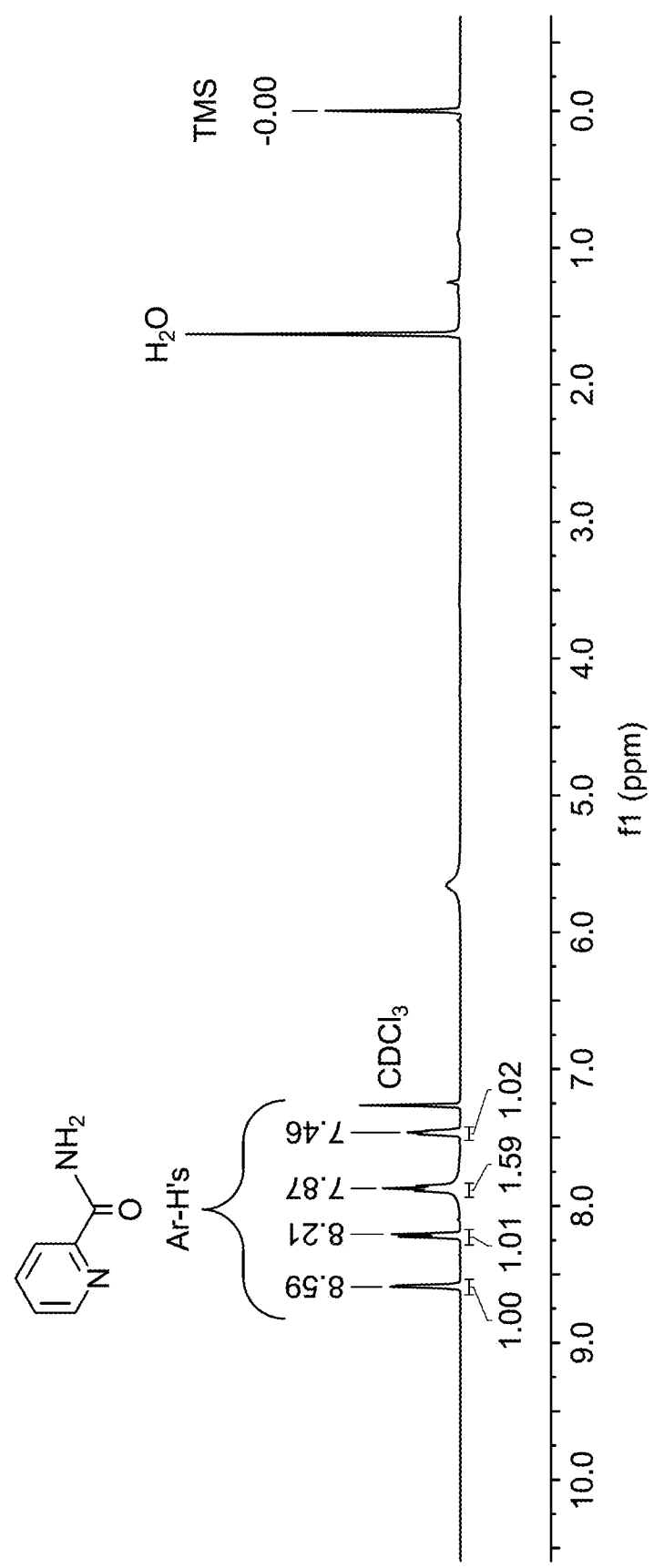
FIG. 14G is $^1H$ NMR spectra of picolinamide, according to certain embodiments.
Figure 14H:
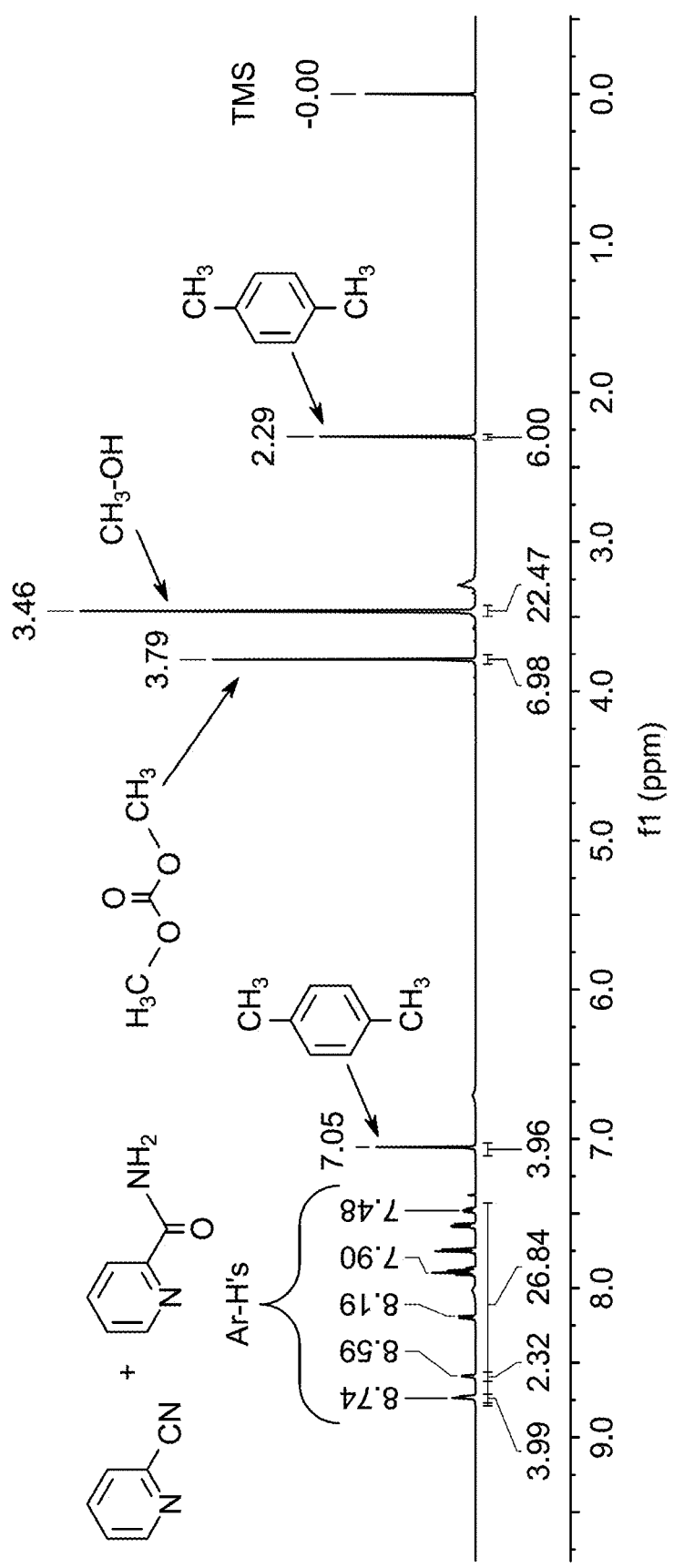
FIG. 14H is $^1H$ NMR spectra of N-$CeO_2$-NR catalyzed reaction after 2 h at 100° C., according to certain embodiments.
Figure 14I:
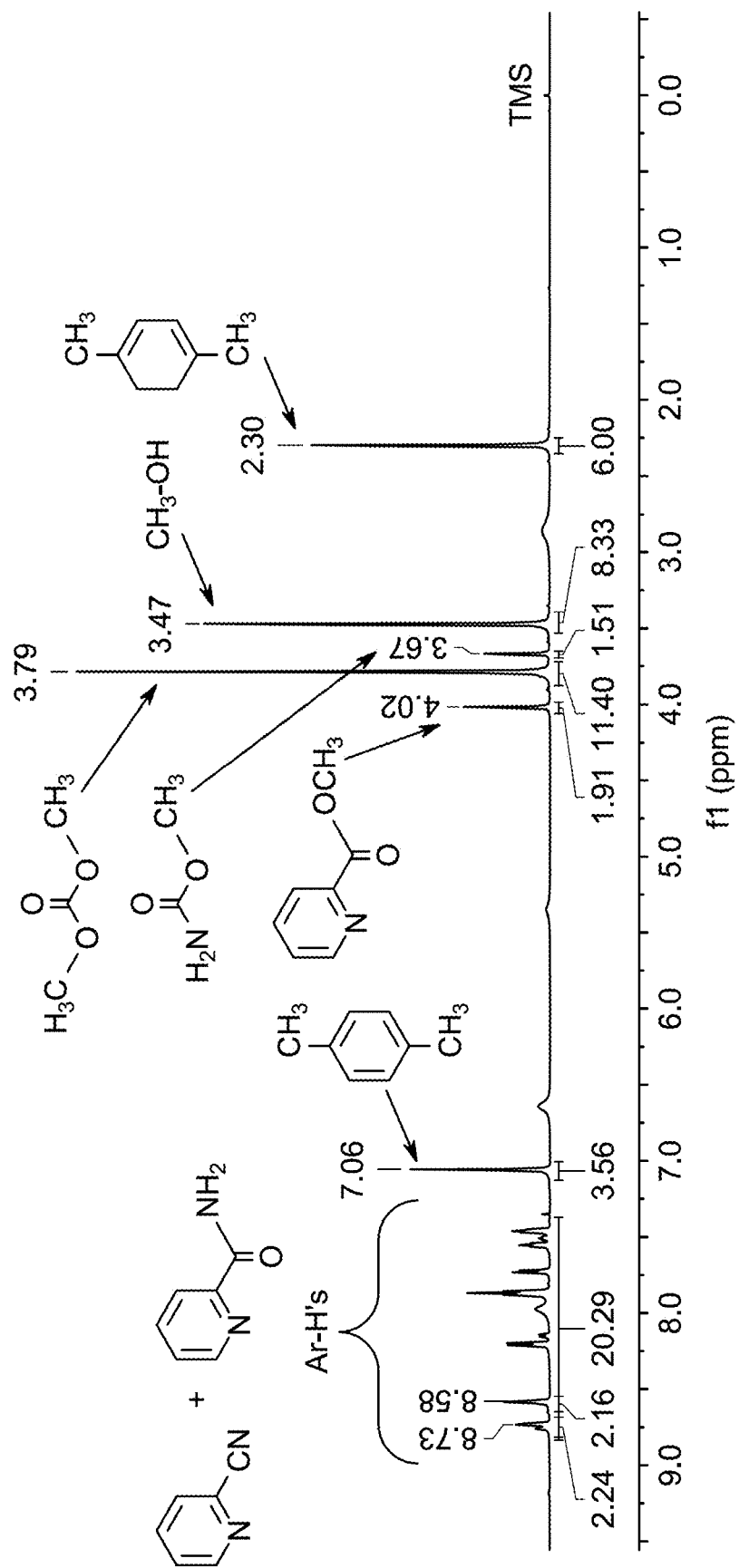
FIG. 14I is $^1H$ NMR spectra of N-$CeO_2$-NR catalyzed reaction after 2 h at 160° C., according to certain embodiments.
Figure 15A:
FIG. 15A is the proposed route towards the formation of side product methyl picolinate during the synthesis of DMC from $CO_2$ and methanol in the presence of 2-cyano pyridine, according to certain embodiments.
Figure 15B:
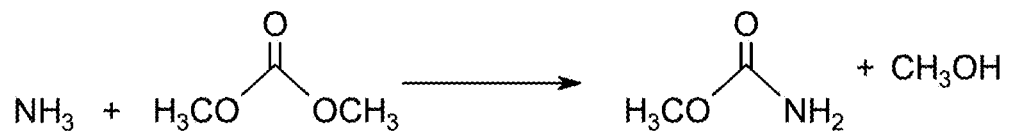
FIG. 15B is the proposed route towards the formation of side product methyl carbamate during the synthesis of DMC from $CO_2$ and methanol in the presence of 2-cyano pyridine, according to certain embodiments.

Next, the effect of reaction temperature on the yield and selectivity of DMC was examined (FIG. 13, Table 8). It was found that a rise in temperature from 100 to 140° C. increases the yield from 113.3 to 242.7 mmol gat, while a further elevation in temperature to 160° C. reduces the yield of DMC (FIG. 13). Additionally, the selectivity vs temperature plot (FIG. 13) indicates that a rise in the reaction temperature from 100 to 160° C. reduces DMC selectivity from 100% to ~75%. The formation of the side products at elevated temperatures was detected to be methyl picolinate and methyl carbamate as also reported earlier (FIG. 14). The formation of methyl picolinate could be attributed to the reaction between methanol and 2-picolinamide, producing ammonia ($NH_3$) as a co-product (FIG. 15A). While a subsequent reaction of the produced $NH_3$ with DMC yielded methylcarbamate (FIG. 15B). Similarly, a rise in reaction time from 2 to 12 h increases DMC yield from 113.3 to 207.7 mmol gut with a slight decrease in selectivity to ~98% (Table 9). A further increase in reaction time to 24 h reduces the yield and selectivity of DMC to 80.7 mmol gut and 65%, respectively.

TABLE 8

Effect of reaction temperature on the performances of N-CeO$_2$-NR catalyst.

| Entry | Reaction temp. (° C.) | Dehydrating reagent | MeOH conversion (%) | DMC yield (mmol $g_{cat}^{-1}$) | DMC | Selectivity (%) Methyl picolinate | Methyl carbamate |
|---|---|---|---|---|---|---|---|
| 1 | 100 | 2-CP | 22.7 | 113.3 | 100 | 0 | 0 |
| 2 | 120 | 2-CP | 39.6 | 196.7 | 99.2 | 0.5 | 0.3 |
| 3 | 140 | 2-CP | 51.4 | 242.7 | 94.4 | 3 | 2.6 |
| 4 | 160 | 2-CP | 47.9 | 190 | 75.2 | 14.4 | 10.4 |

Reaction conditions: 100 mg catalyst, Methanol (3.20 g, 100 mmol), 2-cyanopyridine (2-CP: 5.20 g, 50 mmol), $CO_2$ (4 MPa), 2 h. The DMC yield and selectivity were estimated using 1H NMR spectra.

TABLE 9

Effect of reaction time on the performances of $N\text{-}CeO_2\text{-}NR$ catalyst.

| Entry | Reaction time (h) | Dehydrating reagent | MeOH conversion (%) | DMC yield (mmol $g_{cat}^{-1}$) | Selectivity (%) DMC | Methyl picolinate | Methyl carbamate |
|---|---|---|---|---|---|---|---|
| 1 | 2 | 2-CP | 22.7 | 113.3 | 100 | 0 | 0 |
| 2 | 12 | 2-CP | 42.4 | 207.7 | 97.9 | 0.7 | 1.4 |
| 3 | 24 | 2-CP | 33.6 | 80.7 | 64.9 | 33.4 | 1.7 |

Reaction conditions: 100 mg catalyst, Methanol (3.20 g, 100 mmol), 2-cyanopyridine (2-CP: 5.20 g, 50 mmol), $CO_2$ (4 MPa), 100° C. The DMC yield and selectivity were estimated using 1H NMR spectra.

Figure 16:
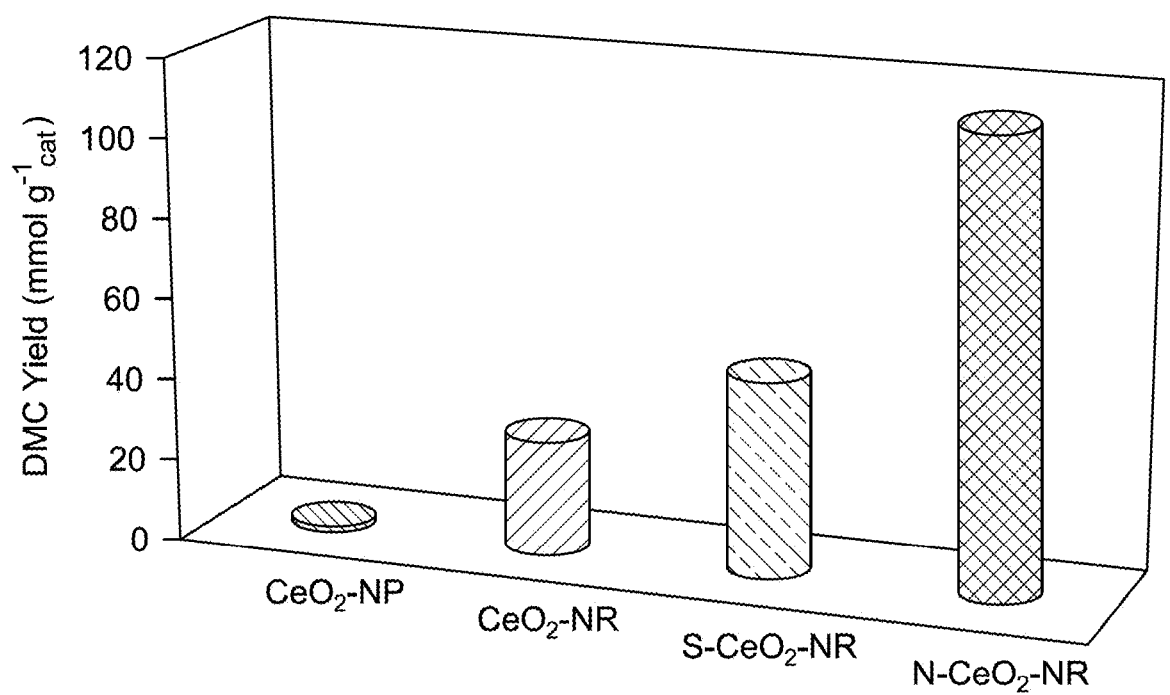
FIG. 16 is a bar graph showing catalytic efficiency of $CeO_2$ nanomaterials towards the yield of DMC from $CO_2$ and methanol, according to certain embodiments.
Figure 17:
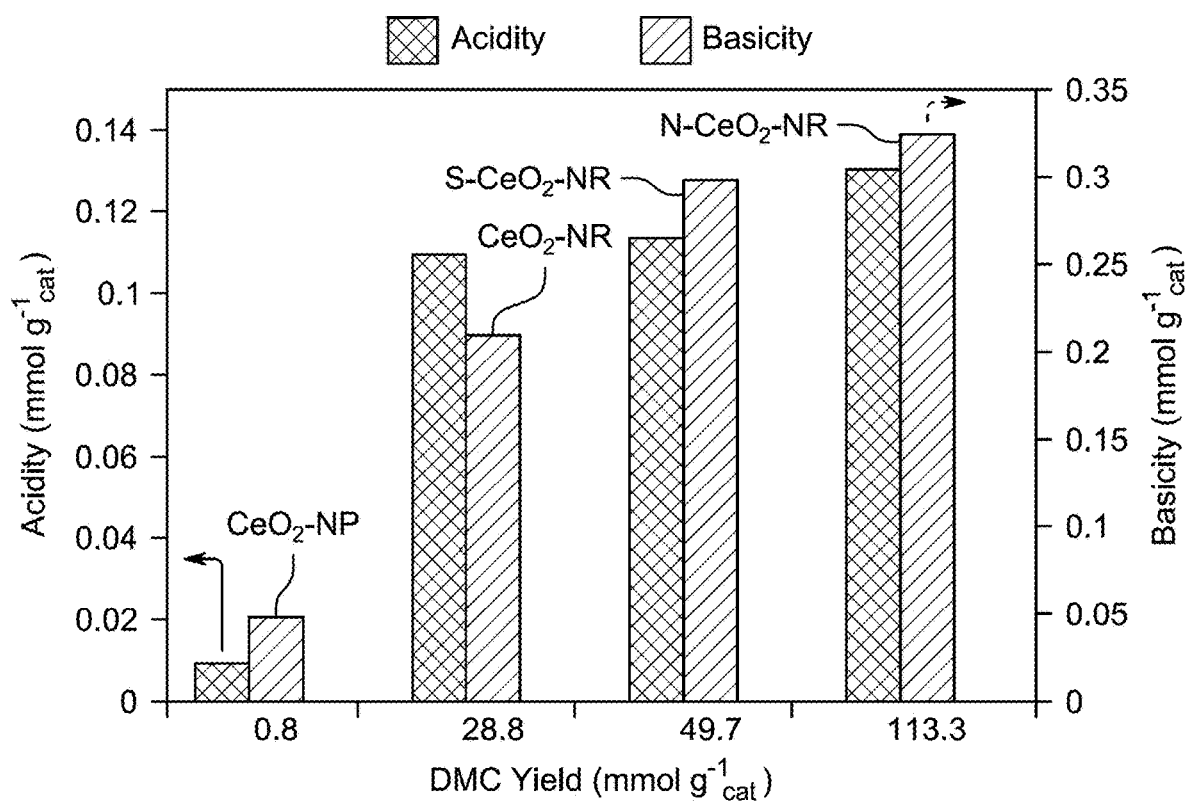
FIG. 17 is a bar graph showing correlation between surface acidity, surface basicity and catalytic efficiency (DMC yield) of the CeO₂ based nanocatalysts, according to certain embodiments.

A comparative analysis of the $X\text{-}CeO_2\text{-}NR$ materials with pristine $CeO_2\text{-}NR$ and $CeO_2\text{-}NP$ was conducted by performing the reaction at 100° C. under a $CO_2$ pressure of 4 MPa (FIG. 16, Table 10). Notably, $N\text{-}CeO_2\text{-}NR$ outperformed all the catalysts, exhibiting the highest DMC yield, while $CeO_2\text{-}NP$ displayed the lowest with catalytic efficiency in the order of $N\text{-}CeO_2\text{-}NR$ (113.3 mmol $g_{cat}^{-1}$)>$S\text{-}CeO_2\text{-}NR$ (49.7 mmol $g_{cat}^{-1}$)>$CeO_2\text{-}NR$ (28.8 mmol $g_{cat}^{-1}$)>$CeO_2\text{-}NP$ (0.8 mmol $g_{cat}^{-1}$). The effects of surface acidity and basicity on the catalytic performance of $CeO_2$ nanomaterials were examined. A plot of total acidity and basicity (Table 5) vs DMC yield (Table 10) of the respective $CeO_2$ nanomaterials indicates that an increase in both acidity and basicity enhances the overall yield (FIG. 17). Note that, the surface areas of all the $X\text{-}CeO_2\text{-}NR$ are similar (Table 2), therefore, the efficiency is unlikely to be affected by this factor for the studied nanorod materials. The excellent efficiency of $N\text{-}CeO_2\text{-}NR$ is attributable to its elevated abundance of $Ce^{3+}$ [%], oxygen vacancy, surface basicity, and acidity, as corroborated by XPS, Raman, $CO_2$ and $NH_3$-TPD analysis data (Table 2, Table 4 and 5). Nonetheless, it is to be mentioned that the commercial material ($CeO_2\text{-}NP$) exhibited the lowest efficiency under identical reaction conditions, primarily due to its least surface area (Table 2), inferior surface acidity and basicity ($NH_3$- and $CO_2$-TPD) (Table 5), as well as a lower $Ce^{3+}$ abundance (%) (Table 2) and oxygen vacancy concentration (Table 4) compared to all $CeO_2$ nanorod materials.

TABLE 10

Comparative catalytic efficiency of $CeO_2$ nanomaterials towards the yield of dimethyl carbonate from $CO_2$ and methanol.

| Entry | Catalysts | Catalyst wt. (mg) | Methanol (mmol) | 2-CP (mmol) | $CO_2$ (MPa) | Temp. (° C.) | Time (h) | MeOH conv. (%) | DMC yield (mmol $g_{cat}^{-1}$) | DMC Selectivity (%) |
|---|---|---|---|---|---|---|---|---|---|---|
| 1 | $CeO_2$- | 100 | 100 | 50 | 4 | 100 | 2 | 0.2 | 0.8 | 100 |
| 2 | $CeO_2$-NR | 100 | 100 | 50 | 4 | 100 | 2 | 5.8 | 28.8 | 100 |
| 3 | $S\text{-}CeO_2$-NR | 100 | 100 | 50 | 4 | 100 | 2 | 9.9 | 49.7 | 100 |
| 4 | $N\text{-}CeO_2$-NR | 100 | 100 | 50 | 4 | 100 | 2 | 22.7 | 113.3 | 100 |

To compare the efficiency of $S-CeO_2-NR$ and $N-CeO_2-NR$ to that of analogous materials reported in the literature the normalized DMC yield (mmol $g_{cat}^{-1}$ $h^{-1}$) with DMC selectivity and the reactions condition data are enlisted in Table 11. Both these catalysts exhibited 100% DMC selectivity under a moderate reaction temperature (100° C.). Further, $N-CeO_2-NR$ exhibited DMC yield (Entry 4) comparable to the highest active system reported (Entry 10).

Figure 18:
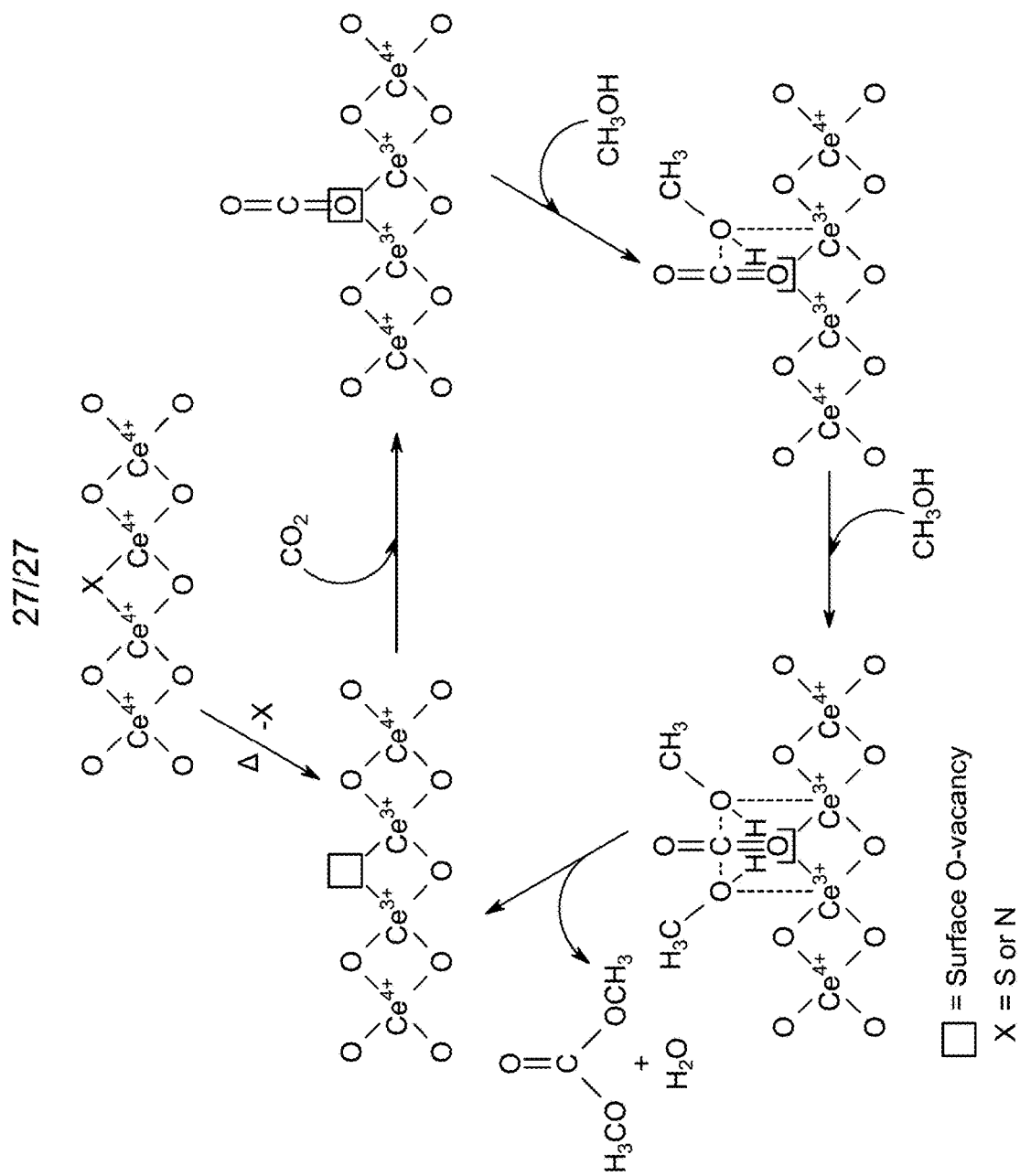
FIG. 18 is the proposed reaction mechanism involving X-CeO₂-NR catalysts towards the synthesis of DMC from CO₂ and methanol, according to certain embodiments.

Based on the catalyst's characterization data and catalysis results for the $X-CeO_2-NR$ catalysts with improved surface acidity-basicity, oxygen vacancies, $Ce^{3+}$ concentration and catalytic efficiency, a tentative reaction mechanism could be proposed in FIG. 18. Initially, under the thermal treatment the as-synthesized $X-CeO_2-NR$ generates surface active sites comprising $Ce^{3+}$ and oxygen vacancies, which are known to induce Lewis acid-base bifunctional sites. The $CO_2$ molecule is activated after the coordination of the non-bonding electron on its oxygen atoms to the vacancy site. Subsequently, the oxygen atom of a methanol molecule is absorbed on $Ce^{3+}$ Lewis acid sites forming methoxy carbonate anion intermediate species ($CH_3OCO^{2-}$). Further, another methanol molecule is proposed to be absorbed on the opposite $Ce^{3+}$ sites. This leads to the formation of DMC and water with simultaneous regeneration of the oxygen vacant site on the catalyst surface.

TABLE 11

Comparative performance of $CeO_2$ nanomaterials towards the yield of dimethyl carbonate from $CO_2$ and methanol.

| Entry | Catalysts | Catalyst wt. (mg) | Methanol (mmol) | 2-CP (mmol) | $CO_2$ (MPa) | Temp. (° C.) | Time (h) | DMC yield (mmol $g_{cat}^{-1}$) | DMC Selectivity (%) | Ref. |
|---|---|---|---|---|---|---|---|---|---|---|
| 1 | $S-CeO_2$-NR | 100 | 100 | 50 | 4 | 100 | 2 | 24.8 | 100 | This work |
| 2 | $N-CeO_2$-NR | 100 | 100 | 50 | 4 | 100 | 2 | 56.7 | 100 | This work |
| 3 | $N-CeO_2$-NR | 100 | 100 | 50 | 4 | 120 | 2 | 98.4 | 99.2 | This work |
| 4 | $N-CeO_2$-NR | 100 | 100 | 50 | 4 | 140 | 2 | 121.4 | 94.4 | This work |
| 5 | $CeO_2$ | 340 | 20 | 100 | 5 | 120 | 16 | 1.8 | 99 | [1] |
| 6 | $CeO_2$-ZnO | 600 | 100 | 50 | 4 | 120 | 12 | 6.6 | 98.9 | [2] |
| 7 | $CeO_2$-$Co_3O_4$ | 100 | 85.5 | 50 | 5 | 120 | 12 | 7.3 | $NR^a$ | [3] |
| 8 | $CeO_2$-Spindle | 100 | 370 | — | 5 | 140 | 2 | 0.004 | $NR^a$ | [4] |
| 9 | $CeO_2$ | 100 | 247 | 57 | 4 | 140 | 5 | 52 | 92.3 | [5] |
| 10 | $CeO_2$ | 100 | 370 | 50 | 5 | 140 | 3 | 126.2 | $NR^a$ | [6] |

[1] Honda, M., et al., Organic carbonate synthesis from $CO_2$ and alcohol over $CeO_2$ with 2-cyanopyridine: Scope and mechanistic studies, *Journal of Catalysis*, Volume 318, 2014, pages 95-107.
[2] Challa, P., et al. Coupling of $CH_3OH$ and $CO_2$ with 2-cyanopyridine for enhanced yields of dimethyl carbonate over ZnO-CeO2 catalyst, *J Chem Sci*, 131, 86, 2019.
[3] He, Z. et al., Synthesis of dimethyl carbonate from $CO_2$ and methanol over $CeO_2$ nanoparticles/$Co_3O_4$ nanosheets, *Fuel*, Volume 325, 2022, 124945.
[4] Wang, S., et al., Morphology control of ceria nanocrystals for catalytic conversion of $CO_2$ with methanol, *Nanoscale*, 2013, 5, 5582-5588.
[5] Yang, G., et al., Investigation of synthesis parameters to fabricate $CeO_2$ with a large surface and high oxygen vacancies for dramatically enhanced performance of direct DMC synthesis from $CO_2$ and methanol, *Mol. Catal.*, 2022, 528, 112471.
[6] Wang, S., et al., Enhancements of dimethyl carbonate synthesis from methanol and carbon dioxide: The in situ hydrolysis of 2-cyanopyridine and crystal face effect of ceria, *Chin. Chem. Lett.*, 2015, 26, 1096-1100, each incorporated herein by reference in their entirety.

The heteroatom (S and N)-modified $CeO_2$ nanorod materials ($S-CeO_2-NR$ and $N-CeO_2-NR$) and pristine $CeO_2-NR$ were developed under a simple hydrothermal thesis protocol. Such an approach is found to influence the acid-base characteristics and the abundance of surface oxygen vacancies within the nanomaterials. This was experimentally substantiated by both $CO_2$- and $NH_3$-TPD, and Raman analyses, respectively. Among all the nanomaterials, $N-CeO_2-NR$ exhibited the highest surface basicity, acidity and oxygen vacancy concentration. Nonetheless, the XPS analysis reveals that $N-CeO_2-NR$ exhibited the highest degree of $Ce^{3+}$ species on the surface. Indeed, operating under identical reaction conditions the N-CeO$_2$-NR showed the highest yield of DMC among all the catalysts studied.

Numerous modifications and variations of the present disclosure are possible in light of the above teachings. It is therefore to be understood that within the scope of the appended claims, the disclosure may be practiced otherwise than as specifically described herein.

The invention claimed is:

1. A method of dimethyl carbonate production, comprising:
reacting CO$_2$ and methanol in the presence of a heteroatom-modified cerium oxide catalyst to form dimethyl carbonate,
wherein the heteroatom-modified cerium oxide catalyst comprises an element selected from the group consisting of N, S and combinations thereof, in an amount ranging from 0.05 to 2 wt. % based on the total weight of the heteroatom-modified cerium oxide catalyst,
wherein the heteroatom-modified cerium oxide catalyst is in the form of nanorods with an average diameter in a range from 1 to 50 nm and an average length in a range from 10 to 700 nm, and
wherein the dimethyl carbonate yield is greater than or equal to 40 mmol·g$_{catalyst}^{-1}$.

2. The method of claim 1, wherein the heteroatom-modified cerium oxide catalyst comprises N in an amount ranging from 0.1 to 0.5 wt. % based on the total weight of the heteroatom-modified cerium oxide catalyst.

3. The method of claim 2, wherein the heteroatom-modified cerium oxide catalyst comprises N in an amount ranging from 0.15 to 0.35 wt. % based on the total weight of the heteroatom-modified cerium oxide catalyst.

4. The method of claim 1, wherein the heteroatom-modified cerium oxide catalyst comprises S in an amount ranging from 0.1 to 1 wt. % based on the total weight of the heteroatom-modified cerium oxide catalyst.

5. The method of claim 4, wherein the heteroatom-modified cerium oxide catalyst comprises S in an amount ranging from 0.15 to 0.5 wt. % based on the total weight of the heteroatom-modified cerium oxide catalyst.

6. The method of claim 1, wherein the dimethyl carbonate yield is greater than or equal to 60 mmol·g$^{-1}$.

7. The method of claim 6, wherein the dimethyl carbonate yield is greater than or equal to 80 mmol·g$^{-1}$.

8. The method of claim 7, wherein the dimethyl carbonate yield is greater than or equal to 100 mmol·g$^{-1}$.

9. The method of claim 8, wherein the dimethyl carbonate yield is greater than or equal to 120 mmol·g$^{-1}$.

10. The method of claim 1, wherein the selectivity for dimethyl carbonate is greater than or equal to 94%.

11. The method of claim 10, wherein the selectivity for dimethyl carbonate is greater than or equal to 97.5%.

12. The method of claim 11, wherein the selectivity for dimethyl carbonate is greater than or equal to 99%.

13. The method of claim 1, wherein the heteroatom-modified cerium oxide catalyst is in the form of nanorods with an average diameter in a range from 5 to 30 nm and an average length in a range from 50 to 500 nm.

14. The method of claim 13, wherein the heteroatom-modified cerium oxide catalyst is in the form of nanorods with an average diameter in a range from 10 to 25 nm and an average length in a range from 75 to 300 nm.

15. The method of claim 1, wherein the Brunauer-Emmett-Teller (BET) surface area of the heteroatom-modified cerium oxide catalyst is greater than or equal to 65 m$^2$/g.

16. The method of claim 15, wherein the BET surface area of the heteroatom-modified cerium oxide catalyst is greater than or equal to 75 m$^2$/g.

17. The method of claim 16, wherein the BET surface area of the heteroatom-modified cerium oxide catalyst is greater than or equal to 85 m$^2$/g.

18. The method of claim 1, wherein the pore volume of the heteroatom-modified cerium oxide catalyst is greater than or equal to 0.4 cm$^3$/g.

19. The method of claim 18, wherein the pore volume of the heteroatom-modified cerium oxide catalyst is greater than or equal to 0.5 cm$^3$/g.

20. The method of claim 19, wherein the pore volume of the heteroatom-modified cerium oxide catalyst is greater than or equal to 0.6 cm$^3$/g.

* * * * *